United States Patent [19]

Peglion et al.

[11] Patent Number: 4,983,740
[45] Date of Patent: Jan. 8, 1991

[54] PROCESS FOR 1,4-DIHYDROPYRIDINE COMPOUNDS

[75] Inventors: Jean L. Peglion, Le Vesinet; Yves M. Gargouil, Paris; Jean P. Vilaine, Chatenay Malabry, all of France

[73] Assignee: Adir et Compagnie, Neuilly-sur-Seine, France

[21] Appl. No.: 386,430

[22] Filed: Jul. 27, 1989

Related U.S. Application Data

[63] Continuation-in-part of Ser. No. 81,303, Aug. 3, 1987, Pat. No. 4,870,091.

[30] Foreign Application Priority Data

Aug. 4, 1986 [FR] France ................................ 86 11260
Jul. 4, 1989 [FR] France ................................ 89 08920

[51] Int. Cl.$^5$ ........................................... C07D 211/86
[52] U.S. Cl. ................................................... 546/321
[58] Field of Search ........................................... 546/321

[56] References Cited

FOREIGN PATENT DOCUMENTS 0125803 4/1984 European Pat. Off. .
0174131 3/1986 European Pat. Off. .

OTHER PUBLICATIONS

Chem. Pharm. Bull., (1980), 28 (9), pp. 2809–2812.
J. Med. Chem., (1986), 29, pp. 1696–1702.

*Primary Examiner*—Jane T. Fan
*Attorney, Agent, or Firm*—Gordon W. Hueschen

[57] ABSTRACT

The invention relates to a process for producing new compounds of formula I:

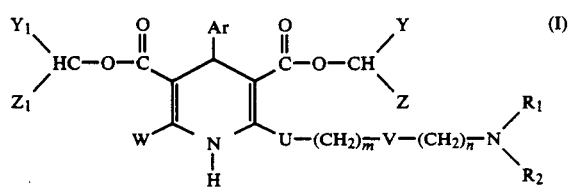

and isomers thereof, as well as acid addition salts thereof, in which the symbols have the meanings set forth in the specification.

1 Claim, No Drawings

PROCESS FOR 1,4-DIHYDROPYRIDINE COMPOUNDS

This application is a continuation in part of our prior-filed copending application Ser. No. 081,303 filed Aug. 3, 1987, now U.S. Pat. No. 4,870,091, issued Sept. 26, 1989.

The present invention relates to new 1,4-dihydropyridine compounds, to the processes for preparing them and to pharmaceutical compositions containing them.

Some 1,4-dihydropyridine compounds such as nifedipine (U.S. Pat. No. 3,485,847) and amlodipine (Publication EP No. 89,167) with useful pharmacological properties, especially as inhibitors of calcium movements across membranes and into cells are known. Other compounds of 2-alkoxymethyl-1,4-dihydropyridine derivatives in which the ether-bound group is substituted with aliphatic or aromatic heterocycles containing one or more nitrogen atoms (Publications EP No. 100,189, EP No. 106,462, EP No. 107,293, EP No. 132,375, EP No. 172,029, EP No. 164,247 and EP No. 150,939) or with aminoalkyl (Publications EP No. 116,769, EP No. 60,674 and EP No. 119,050) or hydroxyalkyl (Publication EP No. 161,917) groups are known.

Moreover, 2-methyl- and 2-aminomethyl-1,4-dihydropyridine compounds are described in Publication EP No. 145,434. Some 2-aminoalkyl-1,4-dihydropyridine compounds are also known (Publication DE No. 2,844,595 and Application JP No. 80/47,656).

The compounds of the present invention are distinguishable from other 1,4-dihydropyridines known in the state of the art, by their structure and by their pharmacological activity. In fact, the compounds of the invention are strong inhibitors of calcium movements across membranes, with a very long lasting activity, thus making it possible to offer treatments with a single daily intake.

More particularly, the present invention relates to 1,4-dihydropyridine compounds of formula I:

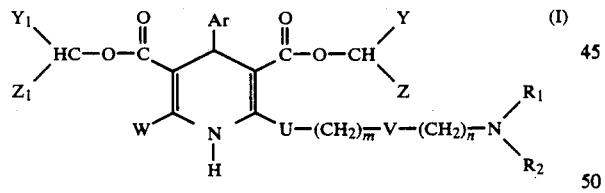

in which:

Ar represents a phenyl radical optionally containing one to five identical or different substituents, each representing a halogen atom, an alkoxy radical containing 1 to 4 carbon atoms, an alkylthio radical containing 1 to 4 carbon atoms, a trihalomethyl radical or a methylenedioxy radical, Y, Z, $Y_1$ and $Z_1$, which may be identical or different, each represent a hydrogen atom, a straight-chain or branched lower alkyl radical containing 1 to 4 carbon atoms, a cyclopropyl radical, a dicyclopropylmethyl radical, a 2,2-dicyclopropylethyl radical, a 2,2-dicyclopropylethenyl radical, a 3,3-dicyclopropylpropyl radical, a 3,3-dicyclopropyl-1-propenyl radical, a straight-chain or branched alkenyl radical containing 2 to 5 carbon atoms or a phenyl radical optionally substituted with a nitro radical, W represents a straight-chain or branched lower alkyl radical containing 1 to 4 carbon atoms or a lower alkoxymethyl radical containing 2 to 5 carbon atoms, V represents a methylene radical or an oxygen atom, U represents a methyleneoxy radical or an ethyleneoxy radical when V represents an oxygen atom, or a methylene radical when V also represents a methylene radical, m and n, which may be identical or different, represent an integer which may take the values from 1 to 4, $R_1$ and $R_2$, which may be identical or different, each represent a hydrogen atom, a straight-chain or branched lower alkyl radical containing 1 to 4 carbon atoms, or a straight-chain or branched lower alkenyl radical containing 2 to 4 carbon atoms, a trihaloacetyl radical, on condition, however, that V never represents a methylene radical in this case, a phenalkyl radical containing 7 to 10 carbon atoms, optionally substituted on the aromatic ring with one or more alkyl or alkoxy radicals containing 1 to 4 carbon atoms or with one or more hydroxy radicals, a 1-hydroxy-2-phenylethyl radical optionally substituted on the aromatic ring with one or more alkyl or alkoxy radicals containing 1 to 4 carbon atoms or with one or more hydroxy radicals or form, together with the nitrogen atom to which they are attached, a phtalimido group, in the racemic form or in the form of optical isomers, and to the addition salts thereof with a pharmaceutically acceptable inorganic or organic acid, and to the quaternary ammonium salts thereof, formed with a lower alkylene or alkyl halide containing 1 to 4 carbon atoms when they contain a tertiary amine.

The present invention also relates to the process for the preparation of the compounds of formula I, wherein:

either a compound of general formula II:

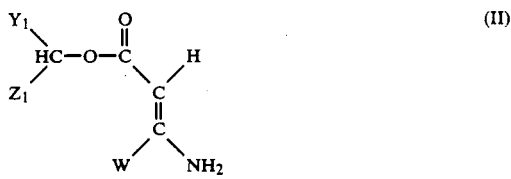

in which the definition of the substituents $Y_1$, $Z_1$ and W remains the same as that defined previously in the case of general formula I, is condensed with a keto ester of general formula III:

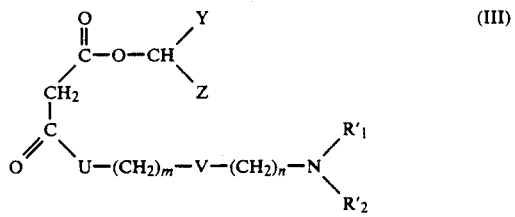

in which Y, Z, U, V, m and n have the meaning defined above in formula I and $R'_1$ and $R'_2$ represent a methyl radical and a benzyl radical, or a hydrogen atom and a trihaloacetyl radical, on condition, however, that V never simultaneously represents a methylene radical in this case, or form, together with the nitrogen atom to which they are attached, a phthalimido radical and with an aromatic aldehyde of general formula IV:

  (IV)

in which the definition of Ar remains the same as that defined previously in the case of general formula I, in a polar organic solvent such as a primary or secondary alcohol or an organic acid, of low molecular weight, and at a temperature between 40° C. and 100° C., so as to obtain a compound of general formula I':

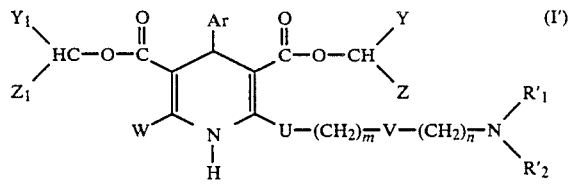  (I')

in which the definition of Ar, Y, Z, $Y_1$, $Z_1$, W, U, V, m and n remains the same as that mentioned above and the definition of $R'_1$ and $R'_2$ remains identical to that given for $R'_1$ and $R'_2$ in general formula III, or a keto ester of general formula V:

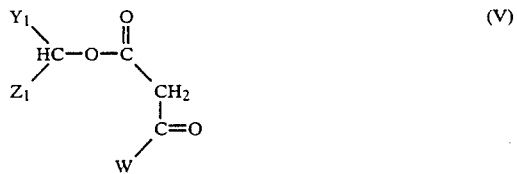  (V)

in which the definition of $Y_1$, $Z_1$ and W remains identical to that given in the case of formula I, is condensed with a compound of general formula VI:

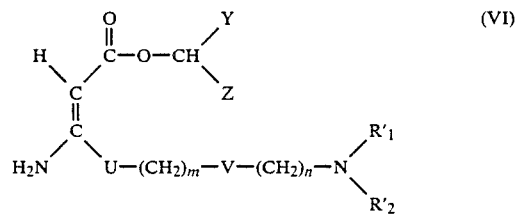  (VI)

in which Y, Z, U, V, m and n have the meaning defined above in the case of formula I, and the definition of $R'_1$ and $R'_2$ remains identical to that given in the case of general formula III and with an aromatic aldehyde of general formula IV, in a polar organic solvent such as a primary or secondary alcohol or an organic acid, of low molecular weight, and at a temperature between 40° and 100° C., so as to obtain a compound of general formula I', or a benzylidene of general formula VII:

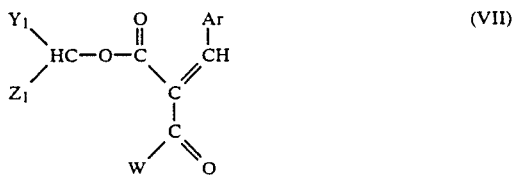  (VII)

in which the definition of $Y_1$, $Z_1$, W and Ar remains identical to that given in the case of formula I, is condensed with a compound of general formula VI, in a polar organic solvent such as a primary or secondary alcohol or an organic acid, of low molecular weight and at a temperature between 40° and 100° C., so as to obtain the compounds of general formula I', and subsequently, the compounds of general formula I' in which the meaning of Ar, Y, Z, $Y_1$, $Z_1$, W, U, V, m and n remains the same as that mentioned above and $R_1$ and $R_2$ represent a hydrogen radical and a trihaloacetyl radical, or form, together with the nitrogen atom to which they are attached, a phthalimido radical, are subjected, if required, to the action of hydrazine or a basic inorganic salt such as potassium carbonate, in the presence of water, in a water-miscible, low molecular weight, polar alcoholic solvent, and at a temperature between 40° and 100° C.

so as to obtain the compounds of general formula I, in which Ar, Y, Z, $Y_1$, $Z_1$, W, U, V, m and n have the meaning defined above and $R_1$ and $R_2$ represent a hydrogen atom, and subsequently, if required, they are either subjected to the action of an arylethylene oxide of general formula VIII:

  (VIII)

in which K represents a phenyl radical, optionally substituted with one or more alkyl or alkoxy radicals containing 1 to 4 carbon atoms or one or more hydroxy radicals, so as to obtain a compound of general formula I":

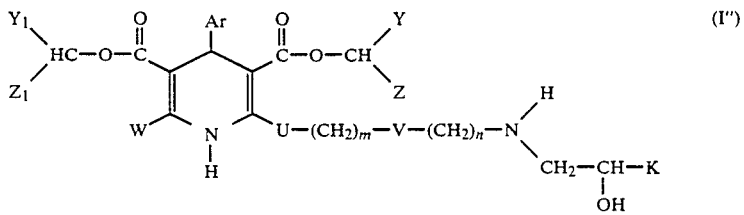  (I")

in which the meaning of Ar, Y, Z, $Y_1$, $Z_1$, W, U, V, m and n remains identical to that mentioned above and the meaning of K remains identical to that given in the case of general formula VIII, or subjected to the action of an alkylating agent of general formula IX:

in which X represents a halogen atom and R represents a straight-chain or branched lower alkyl or alkylene radical containing 1 to 4 carbon atoms, in a polar organic solvent such as acetonitrile, in the presence of a basic inorganic salt such as potassium carbonate, at a temperature between 40° and 100° C., so as to obtain the compounds of general formula I in which Ar, Y, Z, $Y_1$, $Z_1$, W, U, V, m and n have the same meaning as that defined above and $R_1$ and $R_2$ are identical and have the same meaning as R in general formula IX, or alternatively subjected first to the action of benzaldehyde in the presence of an inert and apolar aromatic solvent such as benzene, at a temperature between 50°-120° C., and then, after removing the solvent employed, to the action of sodium borohydride, in the presence of a low molecular weight polar aliphatic alcohol, so as to obtain a compound of general formula I in which the meaning of Ar, Y, Z, $Y_1$, $Z_1$, W, U, V, m and n remains identical to that mentioned above, $R_1$ represents a hydrogen atom and $R_2$ a benzyl radical, which is subsequently subjected, if required, to the action of an alkylating agent of general formula IX, so as to obtain a compound of general formula I in which Ar, Y, Z, $Y_1$, $Z_1$, W, U, V, m and n have the meaning defined above, the definition of $R_1$ is identical to that of R in general formula IX and $R_2$ represents a benzyl radical, in the form of quaternary ammonium or tertiary amine salts, which is subsequently subjected, if required, to the action of lithium triethylborohydride or to a catalytic hydrogenation so as to obtain, with the quaternary ammonium or tertiary amine salts respectively, the compounds of general formula I in which Ar, Y, Z, $Y_1$, $Z_1$, W, U, V, m and n have the same meaning as defined above, $R_1$ having the same meaning as R in general formula IX and $R_2$ representing a benzyl radical or a hydrogen atom respectively, and then it is subjected, if required, to the action of an alkylating agent of general formula IX, so as to obtain the compounds of general formula I, in which $R_1$ and $R_2$, which may be identical or different, each represent a straight-chain or branched lower alkyl radical containing 1 to 4 carbon atoms or a straight-chain or branched alkylene radical containing 1 to 4 carbon atoms and subsequently the compounds of general formula I are converted, if required, into an addition salt with a pharmaceutically acceptable organic or inorganic acid, or, in the case where they carry a tertiary amine in position 2 on their side chain, into a quaternary ammonium salt with a halogenated alkyl or alkylene of general formula IX.

The compounds of general formula II may be obtained according to the method described by CELERIER et al (Synthesis, 1981, p. 130-133).

The compounds of general formula III may be obtained by treating the compounds of general formula X:

$$R'_1 \diagdown N-(CH_2)_n-V-(CH_2)_m-U-C \diagup\!\!\!\diagdown_{OH}^{O} \quad (X)$$

in which U, V, m and n and $R_1'$ and $R_2'$ have the meaning defined above in the case of formula III, with an acid chloride, followed by a condensation with Meldrum's acid in the presence of pyridine so as to obtain the compounds of general formula XI:

$$R'_1 \diagdown N-(CH_2)_n-V-(CH_2)_m-U-C \quad (XI)$$

in which the definition of U, V, m, n, $R'_1$ and $R'_2$ remains identical to that given above. The compounds of general formula XI are then subjected to the action of an alcohol of general formula XII:

$$Y \diagdown CH-OH \diagup Z \quad (XII)$$

in which Y and Z have the meaning defined above in the case of general formula I, at a temperature between 40°-150° C., so as to obtain the compounds of general formula III.

The preparation of the compounds of general formula X is known (Carbohydrate Research, 1981, 88, p. 213-221).

Alternatively, and when, in general formula III, U and V represent an oxygen atom, they may also be prepared according to the method described by C. TROOSTWIJK and R. KELLOGG (J.C.S. Chem. Comm., 1977, p. 932-933).

The compounds of general formula V may also be prepared by the condensation of an acid chloride of general formula XIII:

WCOCL  (XIII)

in which W has the same meaning as in the case of general formula I, with Meldrum's acid. The products resulting from this reaction are then subjected to the action of an alcohol of general formula XII so as to give the compounds of general formula V.

The compounds of general formula VI may be obtained by the action of ammonium acetate on the compounds of general formula III, in a polar alcohol and at a temperature between 50° and 100° C.

The compounds of general formula VII may be obtained by the condensation of the compounds of general formula V with an aromatic aldehyde of general formula IV (Can. J. Chem., 1967, 45, p. 1001).

The process for obtaining secondary amines from quaternary ammonium salts after reacting with lithium triethylborohydride is known (J. Org. Chem. 1975, 40, No. 4, p. 532). Similarly, the alkylation of primary amines with arylethylene oxides of general formula VIII is described in the literature (Tetra. Let. 1986, 27, No. 22, p. 2451-2454).

The optical isomers of the products of general formula I which form the subject of the present invention may be obtained by known methods.

The different processes of separation of isomers or of steroselective synthesis described in the literature do not enable the isomers of 2-{[2-(2-aminoethoxy)ethoxy]-methyl}-4-(2,3-dichlorophenyl)-3ethoxycarbonyl-5-methoxycarbonyl-6-methyl-1,4-dihydropyridine, a compound of general formula I, to be obtained in a good yield. It was hence necessary to invent a new process.

The subject of the present invention is also the process for preparing the (−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine, wherein 2-[2-(2-chloroethoxy)ethoxy]ethanol is condensed with potassium phthalimide, in dimethylformamide in the heated state, to form 2-[2-(2-phtalimidoethoxy)ethoxy]ethanol the compound of the formula XIV:

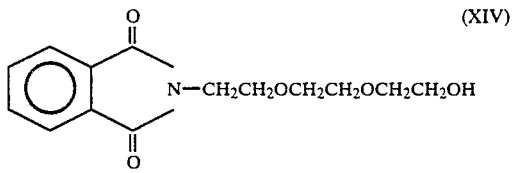
(XIV)

which is converted by means of Jones reagent to 2-[2-(2-phtalimidoethoxy)ethoxy]acetic acid, the compound of the formula XV:

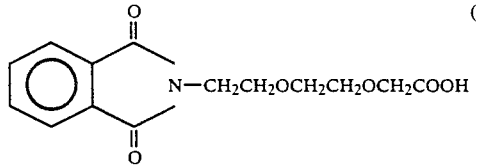
(XV)

which is treated with carbonyldiimidazole and Meldrum's acid in the presence of pyridine in methylene chloride to obtain the compound of formula XVI:

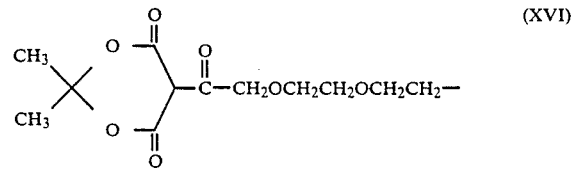
(XVI)

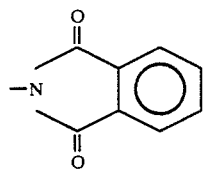

which is then reacted with (R)-2-phenyl-2-methoxyethanol, the compound of formula XVII:

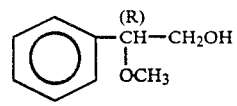
(XVII)

to obtain the β-keto ester of formula XVIII:

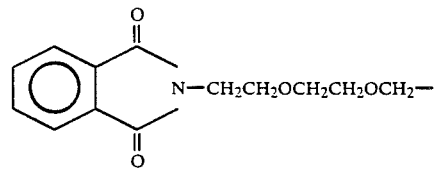
(XVIII)

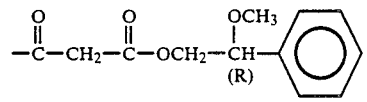

which is condensed in the presence of ammonium formate in ethanol with a benzylidene compound of formula XIX:

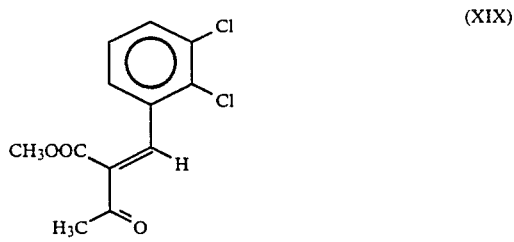
(XIX)

to obtain (4R,4′R/4S,4′R)-4-(2,3-dichlorophenyl)-5-methoxycarbonyl-3-(2-methoxy-2-phenylethoxycarbonyl)-6-methyl-2-{[2-(2-phthalimidoethoxy)ethoxy]-methyl}-1,4-dihydropyridine, the compound of formula XX:

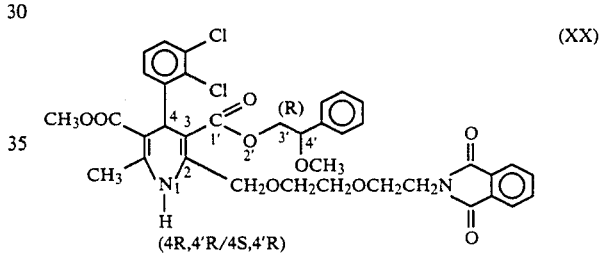
(XX)

and then:
either:
this compound is subjected to the action of aqueous sodium bicarbonate solution, in solution in acetonitrile, to obtain (4R,4′R/4S,4′R)-2-[{2-[2-(2carboxyphenylcarboxamido)ethoxy]ethoxy}methyl]-4-(2,3-dichlorophenyl)-5-methoxycarbonyl-3-(2-methoxy-2-phenylethoxycarbonyl)-6-methyl-1,4-dihydropyridine, the compound of formula XXI:

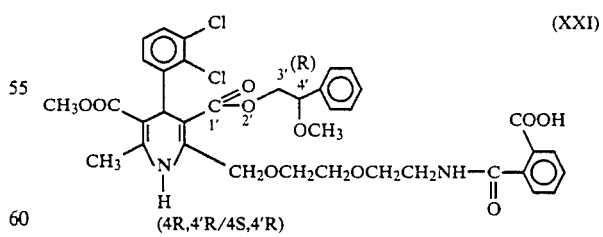
(XXI)

which is treated, after separation by HPLC, with a mixture of glyme and sodium ethylate to obtain a mixture containing (−)-2-[{2-[2-(2-carboxyphenylcarboxamido)-ethoxy]ethoxy}methyl]-4-(2,3-dichlorophenyl)-3-ethoxycarbonyl-5-methoxycarbonyl-6-methyl-1,4-dihydropyridine, the compound of formula XXII:

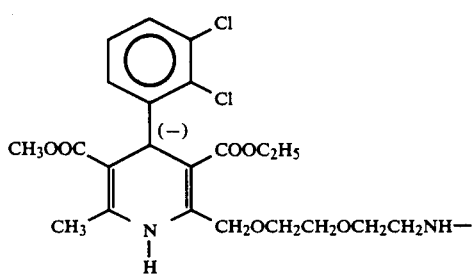

(XXII)

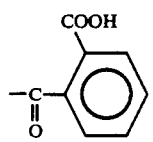

and its homolog substituted at the 5-position with an ethoxycarbonyl radical, or:

the compound of formula xx is separated by chromatography on a silica column, using a mixture of methylene chloride and ethyl acetate (95:5 V/V) as eluant, to obtain the less polar isomer of 4-(2,3-dichlorophenyl)-5-methoxycarbonyl-3-(2-methoxy-2-phenylethoxycarbonyl)-6-methyl-2-{[2-(2-phthalimidoethoxy)ethoxy]-methyl}-1,4-dihydropyridine, which is then subjected to the action of sodium ethanolate in the presence of glyme in solution in ethanol to obtain a mixture containing the compound of formula XXII and its homolog substituted at the 5-position with an ethoxycarbonyl radical, which is then subjected to the action of carbonyldiimidazole in solution in a halogenated alkane at room temperature to obtain a mixture containing (—)-4-(2,3-dichlorophenyl)-3-ethoxycarbonyl-5-methoxycarbonyl-6-methyl-2-{[2-(2-phtalimidoethoxy)ethoxy]methyl}-1,4-dihydropyridine, the compound of formula XXIII:

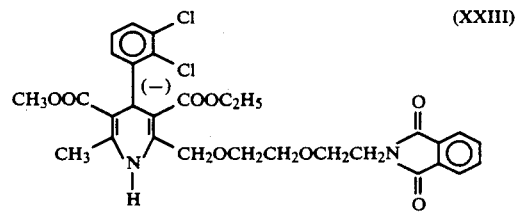

(XXIII)

and its homolog substituted at the 5-position with an ethoxycarbonyl radical, which mixture is then separated by HPLC to obtain pure (—)-4-(2,3-dichlorophenyl)-3-ethoxycarbonyl-5-methoxycarbonyl-6-methyl-2-{[2-(2-phtalimidoethoxy)ethoxy]methyl}-1,4-dihydropyridine, which is then brought to reflux in ethanol in the presence of hydrazine hydrate to give (—)-2-{[2-(2-aminoethoxy)ethoxy]methyl}-4-(2,3-dichlorophenyl)-3-ethoxycarbonyl-5-methoxycarbonyl-6-methyl-1,4-di-hydropyridine, which can then be salified with a pharmaceutically compatible organic or inorganic acid.

(R)-2-Phenyl-2-methoxyethanol, the compound of formula XVII is obtained by reduction of the optically active corresponding acid. The latter compound is prepared according to the process described in J. Chem. Soc. 1962, p. 1519.

2-(2,3-Dichlorobenzylidene)-3-oxobutanoic acid methyl ester, the compounds of formula XIX, is obtained by condensation of 2,3-dichlorobenzaldehyde with methyl acetoacetate.

Among the pharmaceutically acceptable acids for the preparation of the addition salts of the compounds of general formula I, there may be mentioned phosphoric, hydrochloric, citric, oxalic, maleic, sulfuric, tartaric, mandelic, fumaric, methanesulfonic, camphosulfonic, benzenesulfonic, acids and the like.

The compounds according to the invention and the addition or the quaternary ammonium salts thereof are endowed with highly valuable pharmacological properties and are distinguishable form other 1,4-dihydropyridine derivatives which are already known.

In fact, in vitro pharmacological trials have shown that these compounds are strong inhibitors of calcium penetration into cells.

Intracellular calcium concentration plays a messenger role in many biological functions: contractions and secretions; this concentration largely depends on calcium movement across membranes, which, as it is very concentrated in the extracellular media, is conveyed through the calcium-selective channels located in the membrane.

Thus, inhibitors of these channels which restrict or stop the penetration of calcium may have valuable therapeutical effects in many pathological conditions such as vasorelaxation, for the treatment of arterial hypertension and pulmonary hypertension, and peripheral and coronary muscular diseases (Am. J. Card. 1980, 46, p. 1047-1058; Burger's Medicinal Chemistry 4th Edition, Part III, p. 5456—John Wiley and Sons inc. U.S.A., 1981, Life Science, 1983, 33, p. 2571-2581). Induced beneficial effects are also observed in the treatment of cardiac insufficiencies.

The modulation of myocardial contraction is also useful in cardiac ischemic conditions (Medicine, 1985, 64, p. 61-73). The restriction of calcium penetration into cells may also play an important role in preventing calcium accumulation which is characteristic of cell aging and which is related to some vascular degenerative diseases,—atheromatous diseases in particular—(-Medicinal research review, 1985, 5, p. 394-425).

Calcium modulation is also of value in the treatment of epilepsy and dizzinesses of central origin. The restriction of ionized calcium in the smooth fibers of the digestive tract also enables esophageal spasms and, at the pulmonary level, bronchial spasm (treatment of asthma), to be removed. This modulation of ionized calcium may also be useful as adjuvant in the treatment of cancer and that of hypercoagulation.

Moreover, the present description is not limiting; in fact, the fundamental investigations emphasize the primary role played by calcium in many physiological and physiopathological phenomena.

Pharmacological trials in dogs and rats have proved, in vivo, that the activity of the compounds of the invention is at least equal to that of other known 1,4-dihydropyridine compounds, but that they are endowed with a longer-lasting action and confirm their value in therapeutical use. In fact, the different 1,4-dihydropyridine compounds known until now have a short-term activity, which constitutes a considerable disadvantage in human and animal therapeutics.

The invention also extends to pharmaceutical compositions containing, as the active principle, at least one compound of general formula I, one of the optical isomers thereof or one of the addition salts thereof with an inorganic or organic acid or the quaternary ammonium salts thereof, with one or more inert, non-toxic and suitable excipients.

The pharmaceutical compositions thus obtained are advantageously presented in various forms such as, for example, tablets, dragees, capsules, sublingual tablets or other galenical preparations suitable for a sublingual administration, suppositories and injectable or drinkable solutions.

The dosage may vary widely depending on the age and the weight of the patient, the nature and the severity of the condition as well as on whether the administration is through the oral or the parenteral route. In general, the unit dose will range between 0.05 and 50 mg and the daily dose, when administered orally, which can be used in human or animal therapeutics, between 0.05 and 100 mg.

The following examples, given in a non-limiting way, illustrate the invention.

The melting points mentioned are determined according to the micro-Köfler technique.

The proton nuclear magnetic resonance (N.M.R.) spectra were recorded at 60 MHz or 200 MHz.

EXAMPLE 1

(4R,S)-2-{[2-(2-Aminoethoxy)ethoxy]methyl}-3-ethoxycarbonyl-5-methoxycarbonyl-6-methyl-4-pentafluorophenyl-1,4-dihydropyridine hemifumarate Stage A: 10-phthalimido-3-oxo-5,8-dioxadecanoic acid ethyl ester 77 g of 2-[2-(phthalimido)ethoxy]ethanol are added, in portions, to a suspension of 31 g of sodium hydride in 400 ml of tetrahydrofuran, while maintaining the temperature in the vicinity of 25° C. The mixture is stirred for one hour and 53.6 g of ethyl chloroacetoacetate are then added, while maintaining the temperature of the mixture at −20° C. The mixture is allowed to stand overnight at ambient temperature and then hydrolyzed with 1 l of 1N hydrochloric acid. Decantation, followed by extraction with ether are carried out and the organic phases are combined. The combined organic phase is washed with water and then dried over magnesium sulfate. It is concentrated and the residue thereby obtained (110 g) is purified by silica column chromatography using a dichloromethane:acetone (95:5) mixture as the eluting solvent. After removing the eluting solvent, 35.7 g of 10-phthalimido-3-oxo-5,8-dioxadecanoic acid ethyl ester are obtained.

Yield: 30%
Elemental analysis:

|  | C | H | N |
|---|---|---|---|
| Theoretical (%) | 59.49 | 5.82 | 3.85 |
| Found (%) | 59.28 | 5.78 | 3.93 |

Stage B:
(4R,S)-3-Ethoxycarbonyl-5-methoxycarbonyl-6-methyl-4-pentafluorophenyl-2-{[2-(2-phthalimidoethoxy)ethoxy]-methyl}-1,4-dihydropyridine 10.8 g of pentafluorobenzaldehyde are added into a solution of 105 ml of isopropanol containing 20 g of the 10-phthalimido-3-oxo-5,8-dioxadecanoic acid ethyl ester previously obtained and 6.30 g of methyl 2-aminocrotonate.

The mixture is heated under reflux overnight and then evaporated under reduced pressure so as to obtain 39 g of a thick oil. Purification is carried out by silica column chromatography, using a cyclohexane:ethylacetate (80:20) mixture as the eluting solvent. After evaporating off the eluting solvent, recrystallization is carried out twice in methanol so as to obtain 2.3 g of (4R,S)-3-ethoxycarbonyl-5-methoxycarbonyl-6-methyl-4-pentafluorophenyl-2-{[2-(2-phthalimido-ethoxy)ethoxy]methyl}1,4-dihydropyridine.

Yield: 6%
Melting point: 143°–144° C.
Elemental analysis:

|  | C | H | N |
|---|---|---|---|
| Theoretical (%) | 56.43 | 4.26 | 4.38 |
| Found (%) | 56.46 | 4.23 | 4.28 |

Stage C 6.8 g of the compound obtained in the previous stage are dissolved in 68 ml of ethanol containing 2.3 ml of hydrazine hydrate. The mixture is heated under reflux, with stirring, for three hours and then filtered. The filtrate is collected and then evaporated. The residue obtained is dissolved in ethyl ether, filtered and extracted with a 1N sulfuric acid solution. The aqueous phase is made alkaline using concentrated sodium hydroxide and then extracted with ethyl ether. The extract is evaporated to dryness. After recrystallizing the residue in isopropyl ether, 2.3 g of (4R,S)-2-{[2-(2-aminoethoxy)ethoxy]methyl}-3-ethoxycarbonyl-5-methoxycarbonyl-6-methyl-4-pentafluorophenyl-1,4-dihydropyridine are obtained.

Yield: 35%
Melting point: 72°–73° C.

In order to prepare the (4R,S)-2-{[2-(2-aminoethoxy)ethoxy]methyl}-3-ethoxycarbonyl-5-methoxycarbonyl-6-methyl-4-pentafluorophenyl-1,4-dihydropyridine hemifumarate, the quantity of base obtained above is dissolved in a 2% 0.00226M fumaric acid solution. The mixture is heated under reflux in ethanol and then evaporated to dryness and recrystallized in ethanol.

Melting point: 146°–148° C.
Elemental analysis:

|  | C | H | N |
|---|---|---|---|
| Theoretical (%) | 50.89 | 4.81 | 4.95 |
| Found (%) | 50.91 | 4.80 | 4.80 |

The spectral physical constants of (4R,S)-2-{[2-(2-aminoethoxy)ethoxy]methyl}-3-ethoxycarbonyl-5-methoxycarbonyl-6-methyl-4-pentafluorophenyl-1,4-dihydropyridine hemifumarate are given in Table I.

EXAMPLE 2

(4R,S)-2-{[2-(2-Aminoethoxy)ethoxy]methyl}-3-ethoxycarbonyl-5-methoxycarbonyl-6-methyl-4-(2,3-methylenedioxyphenyl)-1,4-dihydropyridine This compound was prepared according to the process described in Example 1, but replacing the pentafluorobenzaldehyde in stage B with 2,3-methylenedioxybenzaldehyde.

Overall yield: 15.5%
Melting point: 98°–100° C.

Elemental analysis:

|  | C | H | N |
| --- | --- | --- | --- |
| Theoretical (%) | 59.73 | 6.54 | 6.06 |
| Found (%) | 59.49 | 6.41 | 5.91 |

The spectral physical constants are given in Table I.

EXAMPLE 3

(4R,S)-2-{[2-(2-Aminoethoxy)ethoxy]methyl}-3-ethoxycarbonyl-5-methoxycarbonyl-6-methyl-4-(2,3,4-trimethoxyphenyl)-1,4-dihydropyridine fumarate This compound was also prepared according to the process described in Example 1, but replacing the pentafluorobenzaldehyde in stage B with 2,3,4-trimethoxybenzaldehyde.

Overall yield: 8.4%
Melting point: 130° C.
Elemental analysis:

|  | C | H | N |
| --- | --- | --- | --- |
| Theoretical (%) | 55.76 | 6.45 | 4.48 |
| Found (%) | 55.83 | 6.60 | 4.81 |

The spectral physical constants of the corresponding base are given in Table I.

EXAMPLE 4

(4R,S)-2-{[2-(2-Aminoethoxy)ethoxy]methyl}-4-(2-chlorophenyl)-3-(2,2-dicyclopropylethoxycarbonyl)-5-methoxycarbonyl-6-methyl-1,4-dihydropyridine fumarate

Stage A: 2,2-Dicyclopropylethyl ester of 10-phthalimido-3-oxo-5,8-dioxadecanoic acid A mixture of approximately 29.5 g of 8-phthalimido-3,6-dioxaoctanoic acid and 155 ml of thionyl chloride is heated under reflux until gas evolution ceases. After cooling, the excess thionyl chloride is removed by distillation and the 31.1 g of acid chloride thus obtained are taken up with benzene. The solvent is evaporated off and the residue is dissolved in 10 ml of methylene chloride. This solution is introduced dropwise into a mixture consisting of 13.6 g of Meldrum's acid, 15.3 ml of pyridine and 75 ml of methylene chloride, while maintaining the temperature between 0° and 5° C. The mixture is allowed to stand for 3 hours at ambient temperature and then diluted with 300 ml of methylene chloride, washed with 100 ml of 1N hydrochloric acid and then with a saturated sodium bicarbonate solution, rinsed with water and dried over anhydrous magnesium sulfate. The organic solvent is evaporated off and the evaporation residue is dissolved in 48 g of 2,2-cyclopropylethanol. A few mg of malonic acid are added and the mixture is heated at 145° C. for approximately 5 hours. The excess 2,2-dicyclopropylethanol is then removed by distillation, the residue is taken up with dichloromethane and the solution is washed with a saturated sodium bicarbonate solution and then with water, dried over anhydrous magnesium sulfate and the organic solvent is evaporated off.

The oil obtained after evaporation is purified by silica column chromatography, using a dichloromethane:ethyl acetate (95:5) mixture as the eluting solvent.

5.7 g of 2,2-dicyclopropylethyl ester of 10-phthalimido-3-oxo-5,8-dioxadecanoic acid are obtained.

Yield: 12.5%
Elemental analysis:

|  | C | H | N |
| --- | --- | --- | --- |
| Theoretical (%) | 65.00 | 56.59 | 316 |
| Found (%) | 64.76 | 6.50 | 3.10 |

Proton nuclear magnetic resonance spectrum (CDCl$_3$): 0.0–0.9 ppm, m, 11H; 3.5 ppm, s, 2H; 3.7 ppm, s, 4H; 3.7–4.0 ppm, m, 4H; 4.0–4.4 ppm, m, 2H; 4.2 ppm, s, 2H; 7.6–8.2 ppm, m, 4H.

Stage B

The (4R,S)-2-{[2-(2-aminoethoxy)ethoxy]methyl}-4-(2-chlorophenyl)-3-(2,2-dicyclopropylethoxycarbonyl)-5-methoxycarbonyl-6-methyl-1,4-dihydropyridine fumarate is obtained by reacting the ester prepared in stage A with 2-chlorobenzaldehyde and methyl 2-aminocrotonate according to the process described in stages B and C of Example 1.

Yield: 10%
Melting point: 198°–199° C.
Mass spectrum of the base (chemical ionization with NH$_3$); 533 m/$_z$ (M$^+$+1), 430 m/$_z$, 428 m/$_z$, 106 m/$_z$.

EXAMPLE 5

(4R,S)-2-{[2-(2-Aminoethoxy)ethoxy]methyl}-4-(2-chlorophenyl)-3-ethoxycarbonyl-5-methoxycarbonyl-6-methyl-1,4-dihydropyridine fumarate This compound was prepared according to the process described in Example 1, but replacing the pentafluorobenzaldehyde with 2-chlorobenzaldehyde.

Yield: 10%
Melting point: 188°–190° C.
Elemental analysis:

|  | C | H | N | Cl |
| --- | --- | --- | --- | --- |
| Theoretical (%) | 54.88 | 5.84 | 4.92 | 6.23 |
| Found (%) | 54.61 | 5.92 | 4.86 | 6.34 |

The spectral physical constants of the corresponding base are given in Table I.

EXAMPLE 6

(4R,S)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine

Stage A: 10-phthalimido-3-oxo-5,8-dioxadecanoic acid ethyl ester 77 g of 2-[2-(phthalimido)ethoxy]ethanol are added, in portions, to a suspension of 31 g of sodium hydride in 400 ml of tetrahydrofuran, while maintaining the temperature in the vicinity of 25° C. The mixture is stirred for one hour and 53.6 g of ethyl chloroacetoacetate are then added, while maintaining the temperature of the mixture at −20° C. The mixture is allowed to stand overnight at ambient temperature and then hydrolyzed with 1 l of 1N hydrochloric acid. Decantation, followed by extraction with ether are carried out and the organic phases are combined. The combined organic phase is washed with water and then dried over magnesium sulfate. It is concentrated and the residue thereby obtained (110 g) is purified by silica column chromatography using a dichloromethane:acetone (95:5) mixture as the eluting solvent.

After removing the eluting solvent, 35.7 g of 10-phthalimido-3-oxo-5,8-dioxadecanoic acid ethyl ester are obtained.

Yield: 30%

Elemental analysis:

|  | C | H | N |
|---|---|---|---|
| Theoretical (%) | 59.49 | 5.82 | 3.85 |
| Found (%) | 59.28 | 5.78 | 3.93 |

Stage B:
(4R,S)-4-(2,3-Dichlorophenyl)-3-ethoxycarbonyl-5-methoxycarbonyl-6-methyl-2-{[2-(2-phtalimidoethoxy)ethoxy]-methyl}-1,4-dihydropyridine 9.7 g of 2,3-dichlorobenzaldehyde are added into a solution of 110 ml of isopropanol containing 20 g of the 10-phtalimido-3-oxo-5,8-dioxadecanoic acid ethyl ester previously obtained and 6.40 g of methyl 2-aminocrotonate.

The mixture is heated under reflux overnight and the evaporated under reduced pressure so as to obtain a thick oil. Purification is carried out by silica column chromatography, using a cyclohexane: ethylacetate (70:30) mixture as the eluting solvent. After evaporating off the eluting solvent, recrystallization is carried out twice in methanol so as to obtain 12.2 g of (4R,S)-4-(2,3-dichlorophenyl)-3-ethoxycarbonyl-5-methoxycarbonyl-6-methyl-2-{[2-(2-phtalimidoethoxy)ethoxy]methyl}-1,4-dihydropyridine.

Yield: 36%

Stage C 12 g of the compound obtained in the previous stage are dissolved in 120 ml of ethanol containing 2.9 ml of hydrazine hydrate. The mixture is heated under reflux, with stirring, for three hours and then filtered. The filtrate is collected and then evaporated. The residue obtained is dissolved in ethyl ether, filtered and extracted with a 1N hydrochloric acid solution. The aqueous phase is made alkaline using concentrated sodium hydroxide and then extracted with ethyl ether. The extract is evaporated to dryness.

Yield: 48%

Melting point: 77°–79° C.

Elemental analysis:

|  | C | H | N | Cl |
|---|---|---|---|---|
| Theoretical (%) | 54.21 | 5.79 | 5.74 | 14/54 |
| Found (%) | 54.32 | 5.74 | 5.72 | 14.67 |

The spectral physical constants thereof are given in Table I.

EXAMPLE 7

(4R,S)-2-[{2-[2-(N-Methyl-N-benzylamino)ethoxy]ethoxy}-methyl]-4-(2-chlorophenyl)-3-ethoxycarbonyl-5-methoxycarbonyl-6-methyl-1,4-dihydropyridine tartrate Stage A:
10-[(N-Methyl-N-benzyl)amino]-3-oxo-5,8-dioxadecanoic acid ethyl ester In order to prepare this compound, the procedure described in Example 1 (Stage A) is used, but the 2-(2-phtalimidoethoxy)ethanol is replaced with 2-[2-(N-methyl-N-benzylamino)ethoxy]ethanol.

Yield: 6.8%

Proton nuclear magnetic resonance spectrum (CDCl₃): 1.3 ppm, t, 3H; 2.3 ppm, s, 3H; 2.6 ppm, t, 2H; 3.4–3.7 ppm, m, 10H; 4.2 ppm, s, 2H; 4.2 ppm, m, 2H; 7.4 ppm, s, 5H.

Stage B:
(4R,S)-2-[{2-[2-(N-Methyl-N-benzylamino)ethoxy]ethoxy}methyl]-3-ethoxycarbonyl-4-(2-chlorophenyl)-5-methoxycarbonyl-6-methyl-1,4-dihydropyridine This base is obtained according to the method described in Example 1 (stage B), but replacing the pentafluorobenzaldehyde with 2-chlorobenzaldehyde and also replacing the 10-phthalimido-3-oxo-5,8-dioxadecanoic acid ethyl ester with the ester obtained in stage A above.

Yield: 40%

The spectral physical constants of this base are given in Table I.

When subjected to the action of tartaric acid, the base described above is converted into tartrate.

Elemental analysis:

|  | C | H | N | Cl |
|---|---|---|---|---|
| Theoretical (%) | 57.74 | 6.08 | 3.96 | 5.01 |
| Found (%) | 58.04 | 6.04 | 3.84 | 5.04 |

EXAMPLE 8

(4R,S)-4-(2-Chlorophenyl)-2-[{2-[2-(N,N-diallylamino)ethoxy]ethoxy}methyl]-3-ethoxycarbonyl-5-methoxycarbonyl-6-methyl-1,4-dihydropyridine hemifumarate 4.5 g of the compound of Example 5 and 1.92 g of allyl bromide are dissolved in 40 ml of acetonitrile, in the presence of 0.0086M of dry potassium carbonate. The mixture is heated under reflux for 16 hours and the precipitate is then filtered, the solvent is evaporated off and the residue is taken up with dichloromethane; the solution is washed with water and evaporated. The residue is chromatographed on a silica column, using a dichloromethane:ethyl acetate (50:50) mixture as eluant so as to obtain pure (4R,S)-4-(2-chlorophenyl)-2-[{2-[2-(N,N-diallylamino)ethoxy]ethoxy}methyl]-3-ethoxycarbonyl-5-methoxycarbonyl-6-methyl-1,4-dihydropyridine (0.7 g).

Yield: 13%

The spectral physical constants of this compound are given in Table I.

The 0.7 g of the compound obtained above is subjected to the action of fumaric acid so as to obtain, after recrystallization in ethanol, 0.4 g of the corresponding hemifumarate.
Melting point: 126°–128° C.
Elemental analysis:

|  | C | H | N | Cl |
|---|---|---|---|---|
| Theoretical (%) | 60.96 | 6.65 | 4.74 | 6.00 |
| Found (%) | 60.94 | 6.57 | 4.71 | 5.96 |

EXAMPLE 9

(4R,S)-2-{[2-(2-Aminoethoxy)ethoxy]methyl}-4-(2-chlorophenyl)-5-(2,2-dicyclopropylethoxycarbonyl)-3-ethoxycarbonyl-6-methyl-1,4-dihydropyridine fumarate The corresponding base is obtained according to the process described in Example 1, but replacing the pentafluorobenzaldehyde with 2-chlorobenzaldehyde and the methyl 2-aminocrotonate with 2,2-dicyclopropylethyl 2-aminocrotonate.
Overall yield: 19%
The spectral physical constants for (4R,S)-2-{[2-(2-aminoethoxy)ethoxy]methyl}-4-(2-chlorophenyl)-5-(2,2-dicyclopropylethoxycarbonyl)-3-ethoxycarbonyl-6-methyl-1,4-dihydropyridine are given in Table I.

3.9 g of this base are dissolved in a 2% solution of fumaric acid in ethanol. The precipitate obtained is recrystallized in methanol so as to obtain 2.7 g of the expected salt.
Melting point: 166°–168° C.
Elemental analysis:

|  | C | H | N | Cl |
|---|---|---|---|---|
| Theoretical (%) | 59.76 | 6.53 | 4.22 | 5.34 |
| Found (%) | 59.75 | 6.80 | 4.15 | 5.44 |

EXAMPLE 10

(4R,S)-2-{[2-(2-Aminoethoxy)ethoxy]methyl}-4-(2,3-dichlorophenyl)-3-ethoxycarbonyl-5-methoxycarbonyl-6-methoxymethyl-1,4-dihydropyridine

Stage A:
2-(2,3-Dichlorobenzylidene)-3-oxo-4-methoxybutanoic acid methyl ester A solution containing 160 ml of anhydrous benzene, 5 g of 2,3-dichlorobenzaldehyde, 4.2 g of 4-methoxy-3-oxobutanoic acid methyl ester, 16 drops of pyridine and 22 drops of hexanoic acid is heated under reflux for one hour, removing the water formed. The mixture is then washed with a saturated sodium bicarbonate solution and then with a 0.1N hydrochloric acid solution. The organic phase is taken and evaporated to dryness so as to obtain 8.3 g of an oil.
Yield: 96.5%
Proton nuclear magnetic resonance spectrum (CDCl$_3$): 3.3–3.4 ppm, d, 3H; 3.7–3.9 ppm, d, 3H; 4.0–4.3 ppm, d, 2H; 7.0–7.7 ppm, m, 3H; 8 ppm, d, 1H.

Stage B:
(4R,S)-2-{[2-(2-Phthalimidoethoxy)ethoxy]methyl}-4-(2,3-dichlorophenyl)-3-ethoxycarbonyl-5-methoxycarbonyl-6-methoxymethyl-1,4-dihydropyridine 8.2 g of the ester from stage A of Example 1, 1.7 g of ammonium acetate and 10 ml of ethanol are heated under reflux for 20 minutes. A solution consisting of 8.2 g of the methyl ester obtained in stage A above and 5 ml of ethanol is then added into the reaction medium. The reaction medium is heated at boiling point for two and a half hours. After evaporation, the residue is taken up with methylene chloride and washed with bicarbonate and then with water. The solution is evaporated to dryness and the oil thereby obtained is purified on a silica column using a cyclohexane:ethyl acetate (70:30) mixture as the eluant. After evaporating off the eluting solvent, 2.7 g of the expected product are obtained.
Yield: 19%
Melting point: 138°–140° C.

Stage C

The process described in stage C of Example 1 is applied to the compound obtained above so as to obtain, after two recrystallizations in isopropyl ether, (4R,S)-2-{[2-(2-aminoethoxy)ethoxy]methyl}-4-(2,3-dichlorophenyl)-3-ethoxycarbonyl-5-methoxycarbonyl-6-methoxymethyl-1,4-dihydropyridine.
Yield: 35%
Melting point: 78°–83° C.
The spectral physical constants are given in Table I.
Elemental analysis:

|  | C | H | N | Cl |
|---|---|---|---|---|
| Theoretical (%) | 53.39 | 5.84 | 5.41 | 13.70 |
| Found (%) | 52.88 | 5.69 | 5.13 | 14.32 |

EXAMPLE 11

N-Benzyl-7-[(4R,S)-3-ethoxycarbonyl-4-(2,3-dichlorophenyl)-5-methoxycarbonyl-6-methyl-2-(1,4-dihydropyridyl)]-N,N-dimethyl-3,6-dioxaheptanammonium iodide

Stage A:
(4R,S)-2-[{2-[2-(N-Benzylamino)ethoxy]ethoxy}-methyl]-4-(2,3-dichlorophenyl)-3-ethoxycarbonyl-5-methoxycarbonyl-6-methyl-1,4-dihydropyridine A mixture consisting of 3.7 g of the compound from Example 6, 0.8 g of benzaldehyde and 10 ml of anhydrous benzene is heated under reflux, removing the water with a suitable apparatus (azeotropic removal water extractor). The organic mixture is evaporated to dryness; the residue is taken up with anhydrous ethanol and 0.3 g of sodium borohydride is added in portions, with intermittent cooling using a cold water bath. The mixture is allowed to stand for 10 minutes with stirring, hydrolysis is carried out on ice, followed by extraction with ethyl ether and then with ethyl acetate so as to obtain 3.2 g of (4R,S)-2-[{2-[2-(N-benzylamino)ethoxy]ethoxy}methyl]-4-(2,3-dichlorophenyl)-3-ethoxycarbonyl-5-methoxycarbonyl-6-methyl-1,4-dihydropyridine.

Stage B 3.9 g of the product above are taken up with 9 ml of dichloromethane in the presence of 1.1 ml of 40% sodium hydroxide and 1.3 ml of methyl iodide. The mixture is allowed to stand overnight, with stirring. The crystals obtained are filtered and then washed with ice-cold water so as to obtain N-benzyl-7-[(4R,S)-3-ethoxycarbonyl-4-(2,3-dichlorophenyl)-5-methoxycarbonyl-6-methyl-2-(1,4-dihydropyridyl)]-N,N-dimethyl-3,6-dioxaheptanammonium iodide.
Yield: 56.8%
Elemental analysis:

|  | C | H | N | Cl | I |
|---|---|---|---|---|---|
| Theoretical (%) | 50.76 | 3.82 | 3.82 | 9.67 | 17.30 |
| Found (%) | 50.44 | 5.31 | 3.62 | 9.35 | 17.18 |

The spectral physical constants of this compound are given in Table I.

EXAMPLE 12

(4R,S)-2-(7-Aminoheptyl)-4-(2-chlorophenyl)-3-ethoxycarbonyl-5-methoxycarbonyl-6-methyl-1,4-dihydropyridine fumarate Stage A: 10-Phthalimido-3-oxo-decanoic acid ethyl ester 10 g of oxalyl chloride are added to a solution consisting of 10.5 g of 8-phthalimidooctanoic acid, 40 ml of anhydrous benzene and 0.2 ml of pyridine. The mixture is heated under reflux for 15 minutes. The solvent is evaporated off, the residue is taken up twice with benzene and an oily compound is separated after filtration. 3.0 g of the acid chloride thus obtained are added to a mixture, which has previously been cooled to 0° C., containing 1.3 g of Meldrum's acid, 1.45 g of pyridine and 8 ml of dichloromethane, while maintaining the temperature at 0° C. The mixture is allowed to stand overnight at ambient temperature, taken up with dichloromethane, washed with 10 ml of 1N hydrochloric acid, dried over anhydrous magnesium sulfate and then evaporated to dryness. The residue is taken up with 2.3 ml of ethanol and the mixture is heated under reflux until gas evolution ceases. After evaporating off the solvent, 2.5 g of 10-phthalimido-3-oxo-decanoic acid ethyl ester crystals are obtained.

Yield: 77%

Elemental analysis:

|  | C | H | N |
|---|---|---|---|
| Theoretical (%) | 66.85 | 9.96 | 3.90 |
| Found (%) | 66.98 | 6.69 | 4.01 |

Stage B:
(4R,S)-4-(2-Chlorophenyl)-3-ethoxycarbonyl-5-methoxycarbonyl-6-methyl-2-(7-phthalimidoheptyl)-1,4-dihydropyridine This compound was prepared starting with the ester obtained in the previous stage, using the preparation process described in Example 1 stage B, but replacing the pentafluorobenzaldehyde with 2-chlorobenzaldehyde.

Stage C

The (4R,S)-2-(7-aminoheptyl)-4-(2-chlorophenyl)-3-ethoxycarbonyl-5-methoxycarbonyl-6-methyl-1,4-dihydropyridine was obtained according to the procedure described in Example 1 stage C.

The spectral physical constants are given in Table I.

This compound is then dissolved in a 2% fumaric acid solution. The solution is evaporated to dryness, the residue is dissolved in acetonitrile and evaporated again. The fumarate obtained is recrystallized in isopropanol.

Yield: 28%

Melting point: 135° C.

Elemental analysis:

|  | C | H | N | Cl |
|---|---|---|---|---|
| Theoretical (%) | 59.51 | 6.60 | 4.95 | 6.27 |
| Found (%) | 59.28 | 6.79 | 4.63 | 5.90 |

EXAMPLE 13

(4R,S)-2-(7-Aminoheptyl)-4-(2-chlorophenyl)-3-(2,2-dicyclopropylethoxycarbonyl)-5-methoxycarbonyl-6-methyl-1,4-dihydropyridine fumarate This compound is obtained according to the method described in Example 12, but replacing the 10-phthalimido-3-oxodecanoic acid ethyl ester with the 2,2-dicyclopropylethyl ester of 10-phthalimido-3-oxodecanoic acid.

Yield: 12%

Melting point: 105°-108° C.

The spectral physical constants of (4R,S)-2-(7-aminoheptyl)-3-(2,2-dicyclopropylethoxycarbonyl)-4-(2-chlorophenyl)-5-methoxycarbonyl-6-methyl-1,4-dihydropyridine are given in Table I.

In order to obtain the corresponding fumarate, salification is carried out with a 2% solution of fumaric acid in ethanol followed by crystallization in acetonitrile.

Melting point: 137°-140° C.

Elemental analysis:

|  | C | H | N | Cl |
|---|---|---|---|---|
| Theoretical (%) | 63.29 | 7.03 | 4.34 | 5.49 |
| Found (%) | 62.67 | 6.91 | 4.45 | 5.05 |

EXAMPLE 14

(4R,S)-2-(5-Aminopentyl)-4-(2-chlorophenyl)-3-ethoxycarbonyl-5-methoxycarbonyl-6-methyl-1,4-dihydropyridine citrate Stage A: 8-Phthalimido-3-oxooctanoic acid ethyl ester This ester is synthesized according to the process described in stage A of Example 4, but replacing the 8-phthalimido-3,6-dioxaoctanoic acid with 6-phthalimidohexanoic acid and the 2,2-dicyclopropylethanol with ethanol.

Stage B and C

The (4R,S)-2-(5-aminopentyl)-4-(2-chlorophenyl)-3-ethoxycarbonyl-5-methoxycarbonyl-6-methyl-1,4-dihydropyridine is obtained according to the processes described in stages B and C of Example 1, but replacing the pentafluorobenzaldehyde in stage B with 2-chlorobenzaldehyde.

Yield: 65%

The spectral physical constants thereof are given in Table I.

In order to obtain the citrate, the base obtained is freeze-dried in the presence of a 0.1N aqueous citric acid solution.

Elemental analysis:

|  | C | H | N | Cl |
|---|---|---|---|---|
| Theoretical (%) | 54.85 | 6.08 | 4.57 | 5.78 |
| Found (%) | 54.85 | 5.97 | 4.54 | 6.11 |

EXAMPLE 15

(4R,S)-2-{[2-(2-Aminoethoxy)ethoxy]methyl}-3,5-diethoxycarbonyl-6-methyl-4-pentafluorophenyl-1,4-dihydropyridine This compound was prepared according to the process described in Example 1, but using ethyl 2-aminocrotonate instead of its methylated homolog in stage B.
Overall yield: 9%
Melting point: 69°–70° C.
Elemental analysis:

|  | C | H | N |
|---|---|---|---|
| Theoretical (%) | 52.87 | 5.20 | 5.36 |
| Found (%) | 52.71 | 5.18 | 5.10 |

The spectral physical constants of this compound are given in Table I.

EXAMPLE 16

(4R,S)-3,5-Diethoxycarbonyl-6-methyl-4-pentafluorophenyl-2-[{2-[2-(N-propylamino)ethoxy]ethoxy}methyl]-1,4-dihydropyridine oxalate

Stage A:
(4R,S)-2-[{2-[2-(N-Benzylamino)ethoxy]ethoxy}methyl]-3,5-diethoxycarbonyl-6-methyl-4-pentafluorophenyl-1,4-dihydropyridine This compound was prepared according to the process described in Example 11, stage A, but using the compound from Example 15 instead of (4R,S)-2-{[2-(2-aminoethoxy)ethoxy]methyl}-4-(2,3-dichlorophenyl)-3-ethoxycarbonyl-5-methoxycarbonyl-6-methyl-1,4-dihydropyridine.

Stage B:
(4R,S)-2-[{2-[2-(N-Benzyl-N-allylamino)ethoxy]-ethoxy}methyl]-3,5-diethoxycarbonyl-6-methyl-4-pentafluorophenyl-1,4-dihydropyridine A mixture containing 1.6 g of the compound obtained in the previous stage, 0.31 g of allylbromide and 0.18 g of potassium carbonate in 20 ml of acetonitrile is heated under reflux, with stirring, overnight. After evaporating off the solvent, the residue is taken up with ether, extracted exhaustively with 0.1N hydrochloric acid, made alkaline in the cold state and then extracted with ethyl acetate so as to obtain, after evaporation, an oil corresponding to the expected structure.

Stage C 0.9 g of the compound obtained above, 0.125 g of oxalic acid and 0.3 g of palladium hydroxide, dissolved in 50 ml of methanol, are subjected to a catalytic hydrogenation at ambient temperature and at atmospheric pressure. After filtering the catalyst, 0.5 g of the expected salt is obtained.
Yield: 54%
Melting point: 151°–153° C.
The spectral physical constants of this salt are given in Table I.

EXAMPLE 17

(4R,S)-2-{[2-(2-Aminoethoxy)ethoxy]methyl}-3-ethoxycarbonyl-5-methoxycarbonyl-6-methyl-4-(2-trifluoromethylphenyl)-1,4-dihydropyridine fumarate This compound was prepared according to the process described in Example 1, stage B and stage C, but using 2-trifluoromethylbenzaldehyde instead of pentafluorobenzaldehyde in stage B.
Yield: 9%
Melting point: 176°–178° C.
Elemental analysis:

|  | C | H | N |
|---|---|---|---|
| Theoretical (%) | 53.82 | 5.52 | 4.64 |
| Found (%) | 53.72 | 5.53 | 4.56 |

The spectral physical constants of the corresponding base are given in Table I.

EXAMPLE 18

(4R,S)-2-{[2-(2-Aminoethoxy)ethoxy]methyl}-4-(3-chlorophenyl)-3-ethoxycarbonyl-5-methoxycarbonyl-6-methyl-1,4-dihydropyridine tartrate This compound was prepared according to the process in Example 1, stages B and C, but replacing the pentafluorobenzaldehyde with 3-chlorobenzaldehyde (stage B) and, in the salification stage (stage C), the fumaric acid with tartaric acid.
Yield: 9.5%
Melting point: 118°–124° C.
The spectral physical constants of this salt are given in Table I.

EXAMPLE 19

(4R,S)-2-{[2-(2-Aminoethoxy)ethoxy]methyl}-3,5-dimethoxycarbonyl-6-methyl-4-pentafluorophenyl-dihydropyridine tartrate This compound was prepared according to the process described in Example 1 (stages B and C), but using 10-phthalimido-3-oxo-5,6-dioxadecanoic acid methyl ester instead of the ethyl ester in stage B and using tartaric acid instead of fumaric acid for the salification.
Yield: 15%
Melting point: 187°–189° C.
Elemental analysis:

|  | C | H | N |
|---|---|---|---|
| Theoretical (%) | 46.59 | 4.53 | 4.34 |
| Found (%) | 46.52 | 4.73 | 4.29 |

The spectral physical constants of (4R,S)-2-{[2-(2-aminoethoxy)ethoxy]methyl}-3,5-dimethoxycarbonyl-6-methyl-4-pentafluorophenyldihydropyridine are given in Table I.

EXAMPLE 20

(4R,S)-2-{[2-(2-Aminoethoxy)ethoxy]methyl}-5-ethoxycarbonyl-3-methoxycarbonyl-6-methyl-4-pentafluorophenyldihydropyridine tartrate This compound was also prepared according to the process described in Example 1, but using ethylcrotonate instead of methylcrotonate in stage B.
Yield: 6%
Melting point: 190°–192° C.
Elemental analysis:

|  | C | H | N |
|---|---|---|---|
| Theoretical (%) | 47.42 | 4.74 | 4.25 |

| | C | H | N |
|---|---|---|---|
| Found (%) | 47.75 | 4.83 | 4.25 |

The spectral physical constants of the corresponding base are given in Table I.

EXAMPLE 21

(4R,S)-2-[{2-[2-(N-Trifluoroacetylamino)ethoxy]-ethoxy}methyl]-3-ethoxycarbonyl-5-methoxycarbonyl-6-methyl-4-pentafluorophenyl-1,4-dihydropyridine In order to obtain this compound, the compound from Example 1 is subjected to the action of triethylamine and trifluoroacetic acid ethyl ester in methanol, at ambient temperature for approximately 48 hours. After filtering the precipitate formed, it is washed with ice-cold methanol (14° C.) and the expected product is obtained in the pure state.

Melting point: 148°–150° C.
Elemental analysis:

| | C | H | N |
|---|---|---|---|
| Theoretical (%) | 47.69 | 4.00 | 4.63 |
| Found (%) | 47.66 | 4.30 | 4.59 |

The spectral physical constants of this base are given in Table I.

EXAMPLE 22

(4R,S)-2-{[2-(2-Aminoethoxy)ethoxy]methyl}-3-ethoxycarbonyl-5-methoxycarbonyl-4-(2-methoxy-3-methylthiophenyl)-1,4-dihydropyridine fumarate This compound was obtained with the synthetic process described in Example 1 (stages B and C), but using 2-methoxy-3-methylthiobenzaldehyde instead of pentafluorobenzaldehyde.

The preparation of the former substance is known (Bull. Soc. Chim. of Japan (1978), 51, (8), p. 2435–2436).
Yield: 13.5%
Melting point: 120° C.
Elemental analysis:

| | C | H | N | S |
|---|---|---|---|---|
| Theoretical (%) | 55.07 | 6.27 | 4.59 | 5.25 |
| Found (%) | 55.11 | 6.14 | 4.42 | 5.32 |

The spectral physical constants of this salt are given in Table I.

EXAMPLE 23

(4R,S)-2-{[2-(2-Aminoethoxy)ethoxy]methyl}-3-(4-nitrobenzyloxycarbonyl)-5-methoxy-6-methyl-4-pentafluorophenyl-1,4-dihydropyridine tartrate

Stage A: 4-Nitrobenzyl ester of 10-phthalimido-3-oxo-5,8-dioxadecanoic acid 35 g of 8-phthalimido-3-6-dioxaoctanoic acid with 18 g of carbonyldiimidazol in 750 ml of a mixture of dimethylformamide and acetonitrile (3:1) are allowed to stand overnight, under nitrogen. 34 g of magnesium 2-(4-nitrobenzyloxycarbonyl)acetate are then added and left to remain in contact for 18 hours. After evaporating off the reaction solvent, the residue is taken up with dichloromethane and washed with water. The residue is then purified on a silica gel column, using a dichloromethane: acetone (95:5) mixture as the eluant, so as to give the expected compound.

Yield: 32.8%

Proton nuclear magnetic resonance spectrum (CDCl$_3$): 3.6 ppm, s, 6H; 3.7–4 ppm, m, 4H; 4.2 ppm, s, 2H; 5.3 ppm, s, 2H; 7.8 ppm, m, 4H; 7.6 ppm, d, 2H; 8.3 ppm, d, 2H.

Stage B

The 2-{[2-(2-aminoethoxy)ethoxy]methyl}-3-(4-nitrobenzyloxycarbonyl)-5-methoxy-6-methyl-4-pentafluorophenyldihydropyridine was prepared according to the process described in Example 1, stages B and C, condensing the compound obtained in the previous stage with pentafluorobenzaldehyde. The spectral physical constants thereof are given in Table I.

Yield: 50%
Elemental analysis:

| | C | H | N |
|---|---|---|---|
| Theoretical (%) | 47.81 | 4.27 | 5.57 |
| Found (%) | 48.04 | 4.19 | 5.29 |

The corresponding salt was obtained after adding a sufficient quantity of tartaric acid dissolved in ethanol.
Melting point: 152°–154° C.

EXAMPLE 24

(4R,S)-2-{[3-(3-Aminopropoxy)propoxy]methyl}-3-ethoxycarbonyl-5-methoxycarbonyl-4-pentafluorophenyl-1,4-dihydropyridine tartrate

Stage A: 12-Phthalimido-3-oxo-5,9-dioxadodecanoic acid ethyl ester

This compound was prepared according to the process described in stage A of Example 1, but using 3-(3-phthalimidopropoxy)propanol.

Proton nuclear magnetic resonance spectrum (CDCl$_3$): 1.3 ppm, t, 3H; 1.6–2.2 ppm, m, 4H; 3.3–4.0 ppm, m, 10H; 4.1 ppm, s, 2H: 4.2 ppm, q, 2H; 7.7–8.3 ppm, m, 4H.

Stage B

The 2-{[3-(3-aminopropoxy)propoxy]methyl}-3-ethoxycarbonyl-5-methoxycarbonyl-4-pentafluorophenyl-1,4-dihydropyridine was prepared according to the process described in Example 1, stages B and C, using the compound obtained above.

The spectral physical constants thereof are given in Table I.

The corresponding tartrate was formed after adding a sufficient quantity of tartaric acid.

Yield: 11%
Melting point: 104° C.
Elemental analysis:

| | C | H | N |
|---|---|---|---|
| Theoretical (%) | 48.98 | 5.14 | 4.08 |
| Found (%) | 48.73 | 5.12 | 4.08 |

EXAMPLE 25

(4R,S)-2-{[2-(2-Aminoethoxy)ethoxy]methyl}-4-(2,3-dichlorophenyl)-3-isopropoxycarbonyl-5-methoxycarbonyl-6-methyl-1,4-dihydropyridine fumarate Stage A: 10-Phthalimido-3-oxo-5,8-dioxadecanoic acid isopropyl ester This compound was prepared according to the process described in Example 4, stage A, but using isopropyl alcohol instead of 2,2-dicyclopropylethanol.

Yield: 67%

Proton nuclear magnetic resonance spectrum (CDCl$_3$): 1.3 ppm, d, 6H; 3.5 ppm, s, 2H, 3.7 ppm, s, 4H; 3.7–4.2 ppm, m, 4H; 4.2 ppm, s, 2H; 4.8–5.4 ppm, m, 1H; 7.6–8.2 ppm, m, 4H.

Stage B

The (4R,S)-2-{[2-(2-aminoethoxy)ethoxy]methyl}-4-(2,3-dichlorophenyl)-3-isopropoxycarbonyl-5-methoxycarbonyl-6-methyl-1,4-dihydropyridine was prepared starting with the compound obtained in the previous stage and with 2,3-dichlorobenzaldehyde according to the process described in Example 1, stages B and C. The spectral physical constants thereof are given in Table I.

Yield: 17.5%

This base was then salified with fumaric acid so as to form the corresponding salt.

Melting point: 106° C. (decomposition)

Elemental analysis:

|  | C | H | N | Cl |
| --- | --- | --- | --- | --- |
| Theoretical (%) | 51.58 | 5.66 | 4.63 | 11.71 |
| Found (%) | 51.47 | 5.39 | 4.40 | 11.74 |

EXAMPLE 26

(4R,S)-2-{[2-(2-Aminoethoxy)ethoxy]methyl}-3-isopropoxycarbonyl-5-methoxycarbonyl-6-methyl-4-pentafluorophenyl-1,4-dihydropyridine tartrate The corresponding base was prepared according to the process described in the previous example, but using pentafluorobenzaldehyde instead of 2,3-dichlorobenzaldehyde.

Yield: 9%

Melting point: 56.9° C.

The (4R,S)-2-{[2-(2-aminoethoxy)ethoxy]methyl}-3-isopropoxycarbonyl-5-methoxycarbonyl-6-methyl-4-pentafluorophenyl-1,4-dihydropyridine tartrate was formed after adding a sufficient quantity of DL-tartaric acid dissolved in ethanol.

Elemental analysis:

|  | C | H | N |
| --- | --- | --- | --- |
| Theoretical (%) | 48.21 | 4.94 | 4.16 |
| Found (*) (%) | 47.53 | 5.02 | 4.06 |

(*) Results corrected for 2.3% of water.

The spectral physical constants of the base are given in Table I.

EXAMPLE 27

(4R,S)-2-{[3-(3-Aminopropoxy)propoxy]methyl}-4-(2,3-dichlorophenyl)-3-ethoxycarbonyl-5-methoxycarbonyl-6-methyl-1,4-dihydropyridine fumarate This compound was prepared according to the process described in Example 24, but using 2,3-dichlorobenzaldehyde instead of pentafluorobenzaldehyde, and a 2% solution of fumaric acid in ethanol instead of tartaric acid for the salification. The spectral physical constants of the base are given in Table I.

Yield: 25%

Melting point: 131°–133° C.

Elemental analysis:

|  | C | H | N | Cl |
| --- | --- | --- | --- | --- |
| Theoretical (%) | 53.25 | 5.74 | 4.43 | 11.22 |
| Found (%) | 53.19 | 5.77 | 4.45 | 11.23 |

EXAMPLE 28

(4R,S)-2-{[2-(2-Aminoethoxy)ethoxy]methyl}-4-(2,3-dichlorophenyl)-3-isobutyloxycarbonyl-5-methoxycarbonyl-6-methyl-1,4-dihydropyridine fumarate Stage A: 10-Phthalimido-3-oxo-5,8-dioxadecanoic acid isobutyl ester This compound was prepared according to the process described in Example 4, stage A, but using isobutyl alcohol instead of 2,2-dicyclopropylethanol.

Yield: 55%

Proton nuclear magnetic resonance spectrum (CDCl$_3$): 0.9 ppm, d, 6H; 1.5–2.4 ppm, m, 1H; 3.6 ppm, s, 2H; 3.5–4.2 ppm, m, 8H; 4 ppm, d, 2H; 4.2 ppm, s, 2H; 7.5–8 ppm, m, 4H.

Stage B

The (4R,S)-2-{[2-(2-aminoethoxy)ethoxy]methyl}-4-(2,3-dichlorophenyl)-3-isobutyloxycarbonyl-5-methoxycarbonyl-6-methyl-1,4-dihydropyridine fumarate was prepared starting with the compound obtained in the previous stage and according to the process described in Example 25, stage B. The spectral physical constants thereof are given in Table I.

Yield: 17%

Melting point: 130° C.

Elemental analysis:

|  | C | H | N |
| --- | --- | --- | --- |
| Theoretical (%) | 53.25 | 5.74 | 4.43 |
| Found (%) | 53.06 | 5.54 | 4.41 |

EXAMPLE 29

(4R,S)-2-{[2-(2-Aminoethoxy)ethoxy]methyl}-4-(2,3-dichlorophenyl)-3-{[(E)-4,4-dicyclopropyl-2-butene]oxycarbonyl}-5-methoxycarbonyl-6-methyl-1,4-dihydropyridine tartrate Stage A: (E)-4,4-dicyclopropyl-3-butenoic acid ethyl ester A mixture containing 0.383 mole of 2,2-dicyclopropylacetaldehyde and 0.574 mole of (carbethoxymethylene)triphenylphosphorane in 800 ml of toluene is heated under reflux for 24 hours. After removing the precipitate formed, the solvent is evaporated off and the residual oil is dissolved in 1575 ml of dimethylformamide. After adding 1575 ml of 3N sulfuric acid, the reaction medium is extracted with 3 liters of hexane. The organic phase is then dried and evaporated to dryness so as to obtain the ester expected.

Yield: 79%

Proton nuclear magnetic resonance spectrum (CDCl$_3$): 0.0–1.4 ppm, m, 11H; 1.5 ppm, t, 3H; 6 ppm, d, 1H; 7.1 ppm, d, 1H.

Stage B: (E)-4,4-Dicyclopropyl-3-buten-1-ol 656 ml of a 1.5M solution of isobutyl aluminum hydride in toluene is cooled to 0° C. and 68.5 g of the ester obtained in the previous stage are added slowly. The mixture is allowed to stand overnight at ambient temperature and is hydrolyzed first with 500 ml of a toluene:methanol (1:1) mixture and then with 1 l of 1N hydrochloric acid. After distillation, the expected alcohol is obtained.

Yield: 75%

Proton nuclear magnetic resonance spectrum (CDCl$_3$): 0–1.5 ppm, m, 11H; 1.5–2 ppm, m, 1H; 4.0–4.3 ppm, m, 2H; 5.6–5.9 ppm, m, 15H.

Stage C: (E)-4,4-Dicyclopropyl-2-butenyl ester of 10-phthalimido-3-oxo-5,8-dioxadecanoic acid This compound was prepared according to the process described in Example 4, stage A, using the alcohol obtained in the previous stage.

Yield: 50%

Stage D

The (4R,S)-2-{[2-(2-aminoethoxy)ethoxy]methyl}-4-(2,3-dichlorophenyl)-3-{[(E)-4,4-dichloropropyl-2-butenyl]oxycarbonyl}-5 methoxycarbonyl-6-methyl-1,4-dihydropyridine was obtained using the ester prepared in the previous stage and according to the process described in Example 1, stages B and C.

The spectral physical constants of this base are given in Table I.

After salification with DL-tartaric acid, the corresponding tartrate is obtained in the solid form.

Yield: 18%

Melting point: 146° C.

Elemental analysis:

|  | C | H | N | Cl |
|---|---|---|---|---|
| Theoretical (%) | 54.91 | 5.96 | 3.78 | 9.53 |
| Found (%) | 54.50 | 5.94 | 3.69 | 9.59 |

EXAMPLE 30

(4R,S)-2-{[3-(3-Aminopropoxy)propoxy]methyl}-3-ethoxycarbonyl-5-methoxycarbonyl-6-methyl-4-(2-methylthio-3-trifluoromethylphenyl)-1,4-dihydropyridine fumarate Stage A: 2-Chloro-3-trifluoromethylbenzaldehyde A solution of 0.6 mole of 2-chlorotrifluoromethylbenzene in 1 l of tetrahydrofuran is cooled to −65° C. and 0.58 mole of butyllithium dissolved in hexane is added. The mixture is maintained at the same temperature for 2 hours and a mixture containing 44 ml of dimethylformamide and 200 ml of tetrahydrofuran is then added dropwise. The reaction medium is allowed to return to ambient temperature, 600 ml of water are added, extraction is then carried out with ethyl ether followed by evaporation to dryness. The product is distilled to purify.

Yield: 40%

Proton nuclear magnetic resonance spectrum (CDCl$_3$): 7.5–7.9 ppm, m, 2H; 8.0–8.4 ppm, m, 2H.

Stage B: 2-Methylthio-3-trifluoromethylbenzaldehyde 0.45 mole of the aldehyde obtained in the previous stage, dissolved in 250 ml of dimethylformamide, is added to a suspension containing 0.45 mole of sodium-methyl sulfide. The medium is heated to 55° C., allowed to return to ambient temperature, hydrolyzed with 500 ml of water, extracted with ether, dried and distilled to obtain the expected aldehyde.

Yield: 30%

Proton nuclear magnetic resonance spectrum (CDCl$_3$): 2.4 ppm, s, 3H; 7.4–8.3 ppm, m, 3H; 10.9 ppm, s, 1H.

Stage C

The (4R,S)-2-{[3-(3-aminopropoxy)propoxy]methyl}-3-ethoxycarbonyl-5-methoxycarbonyl-6-methyl-4-(2-methylthio-3-trifluoromethylphenyl)-1,4-dihydropyridine was prepared according to the process described in Example 1, stages B and C, using the aldehyde described above. The corresponding salt was obtained using a sufficient quantity of fumaric acid. The physical constants of this compound are described in Table I.

Yield: 15%

Melting point: 158° C.

Elemental analysis:

|  | C | H | N | S |
|---|---|---|---|---|
| Theoretical (%) | 53.25 | 5.81 | 4.14 | 4.74 |
| Found (%) | 52.59 | 5.58 | 3.59 | 4.72 |

EXAMPLE 31

(4R,S)-2-{[2-(2-Aminoethoxy)ethoxy]methyl}-3-ethoxycarbonyl-5-methoxycarbonyl-6-methyl-4-(2,3,5-trichlorophenyl)-1,4-dihydropyridine fumarate This compound was obtained according to the process described in Example 1, stages B and C, using 2,3,5-trichlorobenzaldehyde and a sufficient quantity of fumaric acid.

Yield: 21%

Melting point: 114° C.

Elemental analysis:

|  | C | H | N | Cl |
|---|---|---|---|---|
| Theoretical (%) | 48.95 | 4.89 | 4.39 | 16.67 |
| Found (%) | 48.77 | 4.78 | 3.99 | 16.86 |

The spectral physical constants of the compound are given in Table I.

EXAMPLE 32

(4R,S,)-2-{[2-(2-Aminoethoxy)ethoxy]methyl}-3-ethoxycarbonyl-5-methoxycarbonyl-6-methyl-4-(2,3,6-trichlorophenyl)-1,4-dihydropyridine fumarate This compound was prepared according to the process described in Example 31, but using 2,3,6-trichlorobenzaldehyde instead of 2,3,5-trichlorobenzaldehyde.

Melting point: 118° C.
Elemental analysis:

|  | C | H | N | Cl |
|---|---|---|---|---|
| Theoretical (%) | 48.95 | 4.89 | 4.39 | 16.67 |
| Found (%) | 48.74 | 4.85 | 4.36 | 17.00 |

The spectral physical constants of the corresponding base are described in Table I.

EXAMPLE 33

(4R,S)-2-{[2-(2-Aminoethoxy)ethoxy]methyl}-4-(2,3-dichlorophenyl)-3-(4,4-dicyclopropylbutyloxycarbonyl)-5-methoxycarbonyl-6-methyl-1,4-dihydropyridine fumarate Stage A: 4,4-Dicyclopropylbutanoic acid ethyl ester 0.298 mole of the ester obtained in stage A of Example 29 is dissolved in 500 ml of ethanol and it is then subjected to a catalytic hydrogenation at ambient temperature and in the presence of palladinized charcoal containing 5% palladium.

Yield: 94.5%

Proton nuclear magnetic resonance spectrum (CDCl$_3$): 1.0 ppm, m, 11H; 1.3 ppm, t, 3H; 1.85 ppm, q, 2H; 2.5 ppm, t, 2H; 4.2 ppm, q, 2H.

Stage B: 4,4-Dicyclopropylbutanol 0.1 mole of the ester obtained in the previous stage, in 400 ml of ethyl ether, is subjected to the action of 0.1 mole of lithium aluminum hydride. Hydrolysis is carried out followed by distillation so as to obtain the expected alcohol.

Yield: 93%

Stage C: 4,4,-Dicyclopropylbutyl ester of 10-phthalimido-3-oxo-5,8-dioxadecanoic acid This compound was prepared according to the process described in Example 4, stage A, but using the alcohol obtained above instead of 2,2-dicyclopropylethanol.

Yield: 48%

Proton nuclear magnetic resonance spectrum (CDCl$_3$): 0.0–0.7 ppm, m, 10H; 1.0–2.0 ppm, m, 5H; 3.5–4.3 ppm, t,+s+m, 14H; 7.6–8.1 ppm, m, 4H.

Stage D

The (4R,S)-2-{[2-(2-aminoethoxy)ethoxy]methyl}-4-(2,3-dichlorophenyl)-3-(4,4-dicyclopropylbutyloxycarbonyl)-5-methoxycarbonyl-6-methyl-1,4-dihydropyridine fumarate was prepared starting with the ester described in stage C above and according to the process described in stages B and C of Example 1.

Yield: 20%

Melting point: 175° C.

Elemental analysis:

|  | C | H | N | Cl |
|---|---|---|---|---|
| Theoretical (%) | 57.38 | 6.23 | 3.93 | 9.96 |
| Found (%) | 57.01 | 6.27 | 3.86 | 9.90 |

The spectral physical constants of the corresponding base are given in Table I.

EXAMPLE 34

(4R,S)-3-Ethoxycarbonyl-5-methoxycarbonyl-6-methyl-4-pentafluorophenyl-2-[{2-[2-(N-propylamino)ethoxy]ethoxy}-methyl]-1,4-dihydropyridine fumarate Stage A:

(4R,S)-3-Ethoxycarbonyl-5-methoxycarbonyl-6-methyl-4-pentafluorophenyl-2-[{2-[2-(N-allyl-N-benzylamino)-ethoxy]ethoxy}methyl]-1,4-dihydropyridine The (4R,S)-3-ethoxycarbonyl-5-methoxycarbonyl-6-methyl-4-pentafluorophenyl-2-[{2-[2-(N-benzylamino)ethoxy]-ethoxy}methyl]-1,4-dihydropyridine was obtained in the form of an oil, by reacting the compound from Example 1 with benzaldehyde according to the process described in Example 11. 0.027 mole of this compound is then heated under reflux overnight, under nitrogen, with 0.027 mole of allyl bromide and 0.0135 mole of potassium carbonate in 200 ml of acetonitrile. After filtration, the reaction solvent is evaporated off, the residue is taken up with water and ethyl ether and the ethereal phase is then exhaustively extracted with 1N hydrochloric acid. The aqueous phase is made alkaline and extracted with ether. The organic phases are dried and evaporated to dryness to obtain the expected compound.

Yield: 57%

Proton nuclear magnetic resonance spectrum (CDCl$_3$): 1.0–1.3 ppm, m, 3H; 2.3 ppm, s, 3H; 2.5–2.8 ppm, t, 2H; 3.0–3.2 ppm, d, 2H; 3.4–3.7 ppm, m+s, 8H+3H; 3.8–4.2 ppm, q, 2H; 4.6 ppm, s, 2H; 4.9–6.1 ppm, m+s+m, 1H+1H+1H; 7.3 ppm, m, 5H; 7.6 ppm, 1H exchangeable.

Stage B

A mixture containing 0.014 mole of the compound obtained in the previous stage and 0.014 mole of oxalic acid in 500 ml of methanol, is subjected to a catalytic hydrogenation in the presence of 3 g of palladium hydroxide at ambient temperature and at atmospheric pressure. After the mixture has been evaporated and made alkaline, the (4R,S)-3-ethoxycarbonyl-5-methoxycarbonyl-6-methyl-4-pentafluorophenyl-2-[{2-[2-(N-propylamino)ethoxy]ethoxy}methyl]-1,4-dihydropyridine is obtained, which is converted into the fumarate thereof.

Yield: 59%

Melting point: 124° C.

Elemental analysis:

|  | C | H | N |
|---|---|---|---|
| Theoretical (%) | 52.25 | 5.29 | 4.20 |
| Found (%) | 51.90 | 5.36 | 4.25 |

The spectral physical constants of the base are given in Table I.

EXAMPLE 35

(4R,S)-2-{[2-(2-Aminoethoxy)ethoxy]methyl}-4-(2-chloro-3-trifluoromethylphenyl)-3-isopropoxycarbonyl-5-methoxycarbonyl-6-methyl-1,4-dihydropyridine tartrate This compound, in the form of the base, was prepared according to the process described in Example 1, stages B and C, using the 2-chloro-3-trifluoromethyl benzaldehyde described in Example 30, stage A, and the isopropyl ester of 10-phthalimido-3-oxo-5,8-dioxadecanoic acid. The spectral physical constants thereof are given in Table I.

After salification, the corresponding tartrate is obtained.

Yield: 16%
Melting point: 135° C.
Elemental analysis:

|  | C | H | N | Cl |
|---|---|---|---|---|
| Theoretical (%) | 49.09 | 5.30 | 4.09 | 5.18 |
| Found (%) | 49.14 | 5.28 | 3.99 | 5.51 |

EXAMPLE 36

(4R,S)-2-{[2-(2-Aminoethoxy)ethoxy]methyl}-4-(2-chloro-3-trifluoromethylphenyl)-3-(4,4-dicyclopropyl-butyloxycarbonyl)-5-methoxycarbonyl-6-methyl-1,4-dihydropyridine fumarate This compound was prepared according to the process described in Example 1, stages B and C, using 2-chloro-3-trifluoromethylbenzaldehyde and the 4,4-dicyclopropylbutyl ester of 10-phthalimido-3-oxo-5,8-dioxadecanoic acid described in Example 33.

Yield: 10%
Melting point: 122° C.
Elemental analysis:

|  | C | H | N | Cl |
|---|---|---|---|---|
| Theoretical (%) | 56.41 | 5.95 | 3.76 | 4.76 |
| Found (%) | 56.05 | 6.02 | 3.76 | 4.81 |

The spectral physical constants of the corresponding base are given in Table I.

EXAMPLE 37

(4R,S)-2-{[2-(2-Aminoethoxy)ethoxy]methyl}-4-(2-chloro-3-trifluoromethylphenyl)-3-{[(E)-4,4-dicyclopropyl-2-butene]oxycarbonyl}-5-methoxycarbonyl-6-methyl-1,4-dihydropyridine fumarate This compound was prepared according to the process described in Example 1, stages B and C, using 2-chloro-3-trifluoromethylbenzaldehyde and the (E)-4,4-dicyclopropyl-2-butenyl ester of 10-phthalimido-3-oxo-5,8-dioxadecanoic acid described in Example 29.

Yield: 13%
Melting point: 122° C.
Elemental analysis:

|  | C | H | N | Cl |
|---|---|---|---|---|
| Theoretical (%) | 56.57 | 5.70 | 3.77 | 4.77 |
| Found (%) | 56.29 | 5.72 | 3.86 | 5.14 |

The spectral physical constants of the corresponding base are given in Table I.

EXAMPLE 38

(4R,S)-2-{[2-(2-Aminoethoxy)ethoxy]methyl}-4-(2-chloro-3-trifluoromethylphenyl)-3-isobutyloxycarbonyl-5-methoxycarbonyl-6-methyl-1,4-dihydropyridine fumarate This compound was also prepared according to the process described in Example 1, stages B and C, using 2-chloro-3-trifluoromethylbenzaldehyde and the isobutyl ester of 10-phthalimido-3-oxo-5,8-dioxadecanoic acid described in Example 28.

Yield: 17%
Melting point: 118° C.
Elemental analysis:

|  | C | H | N | Cl |
|---|---|---|---|---|
| Theoretical (%) | 52.37 | 5.46 | 4.21 | 5.33 |
| Found (%) | 52.16 | 5.39 | 4.21 | 5.55 |

The spectral physical constants of the corresponding base are given in Table I.

EXAMPLE 39

(4R,S)-2-{[2-(2-Aminoethoxy)ethoxy]methyl}-4-(2,3-dichlorophenyl)-3-[(2-methyl-2-propenyl)oxycarbonyl]-5-methoxycarbonyl-6-methyl-1,4-dihydropyridine fumarate Stage A: 2-Methyl-2-propenyl ester of 10-phthalimido-3-oxo-5,8-dioxadecanoic acid This compound was obtained according to the process described in Example 25, stage A, but using 2-methylpropen-2-ol instead of isopropyl alcohol.

Yield: 80%

Proton nuclear magnetic resonance spectrum ($CDCl_3$): 1.75 ppm, s, 3H; 3.55 ppm, s, 2H; 3.65 ppm, s, 4H; 3.5–4 ppm, m, 4H; 4.1 ppm, s, 2H; 4.55 ppm, s, 2H; 4.95 ppm, m, 2H; 7.5–8.0 ppm, m, 4H.

Stage B (4R,S)-2-{[2-(2-Aminoethoxy)ethoxy]methyl}-4-(2,3-dichlorophenyl)-3-[(2-methyl-2-propenyl)oxycarbonyl]-5-methoxycarbonyl-6-methyl-1,4-dihydropyridine fumarate is obtained starting with the ester obtained in the previous stage and with 2,3-dichlorobenzaldehyde and according to the process described in Example 1, stages A and B.

Yield: 21%
Melting point: 116° C.
Elemental analysis:

|  | C | H | N | Cl |
|---|---|---|---|---|
| Theoretical (%) | 53.43 | 5.44 | 4.45 | 11.26 |
| Found (%) | 53.10 | 5.40 | 4.29 | 11.60 |

The spectral physical constants of the corresponding base are given in Table I.

EXAMPLE 40

2-{2-[2-(Aminoethoxy)ethoxy]ethyl}-4-(2,3-dichlorophenyl)-3-ethoxycarbonyl-5-methoxycarbonyl-6-methyl-1,4-dihydropyridine Stage A: 11-Phenyl-3,6,10-trioxaundecanamine 0.25 mole of aminoethoxyethanol is added to 295 ml of tetrahydrofuran containing 0.25 mole of sodium hydride and the mixture is then heated under reflux for 30 min. Sodium 4-oxy-5-phenylpentanesulfonate dissolved in tetrahydrofuran is then added dropwise. The mixture is heated under reflux for approximately 2 hours, hydrolysis is then carried out followed by the addition of 10 ml of concentrated sodium hydroxide, the reaction solvent is evaporated off and the residue is taken up with a water:ethyl ether mixture. The solution is exhaustively extracted with 1N hydrochloric acid, made alkaline, while cooling, with concentrated sodium hydroxide, extracted with ether, dried and evaporated.

Yield: 32%

Proton nuclear magnetic resonance spectrum (CDCl$_3$): 1.9 ppm, m, 2H; 2.7 ppm, t, 2H; 3.3–3.8 ppm, m, 10H; 4.5 ppm, s, 2H; 7.3 ppm, s, 5H.

Stage B:
(11-Phenyl-3,6,10-trioxa-1-undecanyl)phthalimide 0.0395 mole of the amine obtained in the previous stage and 0.0375 mole of phthalic anhydride are heated, with stirring, at 150° C. for 3 hours, removing the water formed. After purification on silica column using a dichloromethane:ethyl acetate (90:10) mixture as the eluting solvent, the expected product is obtained.

Yield: 67%

Proton nuclear magnetic resonance spectrum (CDCl$_3$): 1.7–2.1 ppm, m, 2H; 3.4–4.0 ppm, m, 12H; 4.5 ppm, s, 2H; 7.3 ppm, s, 5H; 7.5–8.0 ppm, m, 4H.

Stage C: 4,7-Dioxa-9-phthalimidononanol 40 ml of acetonitrile containing 0.054 mole of boron trifluoride etherate are added to 90 ml of acetonitrile containing 0.0216 mole of the compound described above and 0.054 mole of sodium iodide. The reagents are allowed to remain in contact for one hour at ambient temperature, the reaction solvent is evaporated off, the residue is taken up with water, extracted with ethyl ether and washed with thiosulfate. After purification on silica column using, at first, dichloromethane and then a dichloromethane:methanol (80:20) mixture as the eluant, the expected product is obtained.

Yield: 28%

Proton nuclear magnetic resonance spectrum (CDCl$_3$): 1.6–2.0 ppm, m, 2H; 2.1–2.6 ppm, 1H exchangeable; 3.5–4.1 ppm, m, 12H; 7.6–8.0 ppm, m, 4H.

Stage D: 11-Phtalimido-3-oxo-6,9-dioxaundecanoic acid ethyl ester

The alcohol obtained in the previous stage is converted into the corresponding acid by Jones oxidation. The acid is then subjected to the action of thionyl chloride, Meldrum's acid and ethanol according to the process described in Example 4, Stage A, to obtain the expected compound.

Stage E

The 2-{2-[2-(2-Aminoethoxy)ethoxy]ethyl}-4-(2,3-dichlorophenyl)-3-ethoxycarbonyl-5-methoxycarbonyl-6-methylpyridine is obtained starting with the ester described in stage D and 2,3-dichlorobenzaldehyde according to the process described in Example 1, stages B and C. The spectral physical constants of this compound are given in Table I.

EXAMPLE 41

2-[2-(2-Phtalimidoethoxy)ethoxy]acetic acid

Stage A: 2-[2-(2-Phtalimidoethoxy)ethoxy]ethanol 188 g of 2-[2-(2-Chloroethoxy)ethoxy]ethanol and 146 g of potassium phtalimide in 700 ml of dimethylformamide are brought to 95° C. for 17 hours.

The mixture is diluted with methylene chloride, washed with saturated sodium chloride solution, dried and evaporated.

It is distilled in a Kugelrohr, b.p. $_{0.05}$ mmHg: 180°–185° C.

Yield: 90%

Proton nuclear magnetic resonance spectrum (Solvent CDCl$_3$): 4H(m) 7.5 to 8 ppm; 12H(m) 3.4 to 4 ppm; 1H (complex exchangeable D$_2$O) 2.5 to 3 ppm.

Stage B 3 g of the alcohol obtained in the preceding stage are dissolved in 150 ml of acetone. Jones reagent is introduced while the temperature is maintained at between 20° and 25° C. The mixture is left to stand for 1 hour at room temperature. It is concentrated, then diluted with methylene chloride and washed with water. It is dried and the solvent is evaporated off to obtain the expected compound.

Melting point: 88°–90° C.

Yield: 90%

Proton nuclear magnetic resonance spectrum (Solvent CDCl$_3$): 1H (complex exchangeable) 8.8 to 9.5 ppm; 4H(m) 7.6 to 8.1 ppm; 2H(s) 4.1 ppm; 8H(m) 3.6 to 4 ppm.

EXAMPLE 42

(R)-2-Phenyl-2-methoxyethanol 72 g of (R)-2-phenyl-2-methoxyacetic acid (prepared according to the method described in J. Chem. Soc., 1962, p. 1519), are reduced with 16.5 g of lithium aluminum hydride in 300 ml of tetrahydrofuran.

The mixture is hydrolysed and the inorganic salts are filtered off, and the residual oil is then distilled in a Kugelrohr. b.p.$_{15\ mmHg}$=105° C.

Yield: 76%

Proton nuclear magnetic resonance spectrum (Solvent CDCl$_3$): 5H(m) 7.35 ppm; 1H(d) 4.35 ppm; 2H(m) 3.65 ppm; 3H(s) 3.3 ppm; 1H (d exchangeable) 2.35 ppm.

Optical rotation in 1% strength solution in ethanol:

| λ (nm) | $[\alpha]^{24°\ C.}$ |
|---|---|
| 589 | −122 |
| 578 | −127 |
| 546 | −145 |
| 436 | −249 |
| 365 | −396 |

EXAMPLE 43

5,8-Dioxa-3-oxo-10-phthalimidodecanoic acid (R)-2-phenyl-2-methoxyethyl ester 20 g of carbonyldiimidazole are added in a single portion to a suspension containing 34.7 g of the compound of Example 41 in 210 ml of methylene chloride.

The mixture is stirred until gaseous evolution has ceased. A mixture consisting of 17.7 g of Meldrum's acid and 9.2 g of pyridine in 70 ml of methylene chloride is then introduced in a rapid dropwise flow. The mixture is stirred overnight under nitrogen.

The mixture is transferred to a separating funnel, washed with N sulfuric acid to acid pH and then once with water and dried, and the solvent is evaporated off.

The oil is taken to a water bath with 25 g of the alcohol obtained in Example 42 until evolution has ceased.

The reaction medium is subjected to chromatography (flash chromatography) on a column containing 1.8 kg of silica, using a mixture of cyclohexane and ethyl acetate (1:1 V/V) as eluant, to obtain the expected compound.

Yield: 70%.

Proton nuclear magnetic resonance spectrum (Solvent CDCl₃): 4H(m) 7.6 to 8.1 ppm; 5H(s) 7.35 ppm; 3H(m) 4 to 4.6 ppm; 2H(s) 4.1 ppm; 10H(m) 3.5 to 4 ppm; 3H(s) 3.3 ppm.

Optical rotation in 1% strength solution in ethanol:

| λ (nm) | $[\alpha]^{21°C}$ |
|---|---|
| 589 | −35.1 |
| 578 | −36.5 |
| 546 | −41.4 |
| 436 | −69.8 |
| 365 | −107.2 |

EXAMPLE 44

2-(2,3-Dichlorobenzylidene)-3-oxobutanoic acid methyl ester

A mixture containing 8.7 g of 2,3-dichlorobenzaldehyde, 5.8 g of methyl acetoacetate, 28 drops of pyridine and 38 drops of hexanoic acid in 280 ml of benzene is brought to reflux with stirring for 4 hours. It is transferred to a separating funnel and washed with 10% strength sodium bicarbonate solution, then with N hydrochloric acid solution and then with water. The mixture is dried and evaporated. The crystals obtained are washed with isopropyl ether.

Yield: 65%

Proton nuclear magnetic resonance spectrum (Solvent CDCl₃): 1H(2s) 8 and 8.05 ppm; 3H(m) 7.1 to 7.8 ppm; 3H(2s) 3.9 and 3.75 ppm; 3H(2s) 2.45 and 2.2 ppm.

EXAMPLE 45

(4R,4'R/4S,4'R)-4-(2,3-Dichlorophenyl)-5-methoxycarbonyl-3-(2-methoxy-2-phenylethoxycarbonyl)-6-methyl-2-{[2-(2-phthalimidoethoxy)ethoxy]methyl}-1,4-dihydropyridine A mixture containing 22.2 g of the compound described in Example 44, 38 g of the compound described in Example 43 and 6.3 g of ammonium formate in 200 ml of ethanol is stirred under nitrogen at 40° C. for 48 hours. The residual medium is evaporated and purified on a column containing 4 kg of silica, using a mixture consisting of methylene chloride and ethyl acetate (9:1 V/V) as eluant.

Proton nuclear magnetic resonance spectrum (Solvent CDCl₃): 2H(m) 7.8 ppm; 2H(m) 7.7 ppm; 7H(m) 7.3 to 7.1 ppm; 1H(t) 7.05 ppm; 1H(s) 5.45 ppm; 2H(m) 4.6 ppm; 11H(m) 3.6 to 4.4 ppm; 3H(2s) 3.6 ppm; 3H(2s) 3.2 and 3.05 ppm; 3H(s) 2.3 ppm; 1H(s) not exchangeable with D₂O, 7.4 ppm.

Optical rotation in 1% strength solution in chloroform:

| λ (nm) | $[\alpha]^{21°C}$ |
|---|---|
| 589 | −13.3 |
| 578 | −13.8 |
| 546 | −15.1 |

EXAMPLE 46

(4R,4'R/4S,4'R)-2-[{2-[2-(2-Carboxyphenylcarboxamido)ethoxy]ethoxy}methyl]-4-(2,3-dichlorophenyl)-5-methoxycarbonyl-3-(2-methoxy-2-phenylethoxycarbonyl)-6-methyl-1,4-dihydropyridine A mixture containing 16.5 g of the compound of Example 45, 100 ml of 10% strength aqueous sodium bicarbonate solution and 230 ml of acetonitrile is brought to reflux with stirring for 24 hours. The solvent is evaporated off and the residue is taken up with water, acidified with N hydrochloric acid and extracted to obtain the expected compound.

Yield: 87%.

Proton nuclear magnetic resonance spectrum (Solvent CDCl₃): 1H(m) 7.9 ppm; 3H(m) 7.5 ppm; 7H(m) 7.4 to 7.15 ppm; 1H(t) 7.05 ppm; 1H(2s) 5.45 ppm; 2H(m) 4.8 ppm; 2H(m) 4.4 to 4.1 ppm; 1H(m) 3.9 ppm; 8H(m) 3.8 to 3.5 ppm; 3H(2s) 3.6 ppm; 3H(2s) 3.2 and 3.05 ppm; 3H(s) 2.3 ppm; 1H(t) 6.55 ppm; 1H (masked signal, exchanged with D₂O) 7.45 ppm; 1H (flat signal) 7 to 5 ppm exchanged with D₂O.

Optical rotation in 1% strength solution in chloroform:

| λ (nm) | $[\alpha]^{21°C}$ |
|---|---|
| 589 | −14.2 |
| 578 | −14.8 |
| 546 | −16.3 |

EXAMPLE 47

Mixture of (−)-2-[{2-[2-(2-carboxyphenylcarboxamido)ethoxy]ethoxy}methyl]-4-(2,3-dichlorophenyl)-3-ethoxycarbonyl-5-methoxycarbonyl-6-methyl-1,4-dihydropyridine and its homolog substituted at the 5-position with an ethoxycarbonyl radical \* First Process The compound of Example 46 is separated into its two isomers by HPLC, using a Lichroprep RP18 50 cm long as column and a mixture of methanol and 0.025M disodium phosphate (55:45 V/V) as eluant, flow rate 10 ml/min.

3 g of the second compound derived from the separation are brought to reflux with 30 ml of glyme and 28.6 ml of a 0.26M solution of sodium ethylate. The mixture is evaporated and the residue is taken up with water, acidified and extracted with ethyl acetate to obtain the expected compounds.

Overall yield: 10%

\* Second Process

Stage A

The compound of Example 45 is chromatographed on a preparative column containing 4 kg of silica, using a mixture of methylene chloride and ethyl acetate (95:5) as eluant. The first compound derived from the separation, which is the less polar, is isolated.

Yield: 20%

Proton nuclear magnetic resonance spectrum (Solvent CDCl₃): 2H(m) 7.8 ppm; 2H(m) 7.7 ppm; 7H(m) 7.4 to 7.1 ppm; 1H(t) 7.05 ppm; 1H(s) 5.45 ppm; 2H(m) 4.4 ppm; 11H(m) 4 to 3.7 ppm; 3H(s) 3.6 ppm; 3H(s) 3.05 ppm; 3H(s) 2.3 ppm; 1H(s) 7.45 ppm (exchangeable with D₂O with difficulty).

Optical rotation in 1% strength solution in chloroform:

| λ (nm) | $[\alpha]^{21°C}$ |
|---|---|
| 589 | −9 |
| 578 | −9.6 |

-continued

| λ (nm) | $[\alpha]^{21°\,C.}$ |
|---|---|
| 546 | −10.4 |

Stage B 3 g of the compound obtained in the preceding stage are brought to reflux with 30 ml of glyme and 28.6 ml of a 0.26M ethanolic solution of sodium ethanolate. The mixture is evaporated and the residue is taken up with water, acidified and extracted with ethyl acetate to obtain the expected compounds.

Yield: 65%

EXAMPLE 48

Mixture of (−)-4-(2,3-dichlorophenyl)-3-ethoxycarbonyl-5-methoxycarbonyl-6-methyl-2-{[2-(2-phthalimidoethoxy)ethoxy]methyl}-1,4-dihydropyridine and its homolog substituted at the 5-position with an ethoxycarbonyl radical 1.9 g of the mixture obtained in Example 47 are dissolved in 30 ml of methylene chloride and 0.9 g of carbonyldiimidazole is added in a single portion. The mixture is left stirred overnight.

The reaction medium is transferred to a separating funnel and washed with 10% strength sodium bicarbonate and then with N hydrochloric acid and with water. The mixture is dried and evaporated to obtain the expected compounds.

Yield: 65%

EXAMPLE 49

(−)-4-(2,3-Dichlorophenyl)-3-ethoxycarbonyl-5-methoxycarbonyl-6-methyl-2-{[2-(2-phthalimidoethoxy)-ethoxy]methyl}-1,4-dihydropyridine The mixture obtained in Example 48 is separated by preparative HPLC, using a Lichroprep RP 18 column 50 cm long and a mixture of ethanol, water and TFA (500:500:1) as eluant. The expected compound is isolated first.

Yield: 30%

Optical rotation in 1% strength solution in DMSO:

| λ (nm) | $[\alpha]^{20°\,C.}$ |
|---|---|
| 589 | −34.6 |
| 578 | −36.5 |
| 546 | −43.9 |
| 436 | −119.0 |

EXAMPLE 50

(−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine 1 g of the compound prepared in Example 49 is refluxed with 10 ml of ethanol and 0.25 ml of hydrazine hydrate for 4 hours. The solvent is evaporated off, the residue is taken up with ethyl ether and washed with 5 ml of normal sodium hydroxide and the ether phase is exhaustively extracted with N hydrochloric acid. The aqueous phases are then alkalinized and extracted with ethyl ether to obtain the expected compound.

Yield: 60%

Melting point: 69°–71° C.

Proton nuclear magnetic resonance spectrum (Solvent CDCl$_3$): 1H(m) 7.3 to 7.7 ppm exchangeable with D$_2$O; 3H(m) 7.6 to 6.9 ppm; 1H(s) 5.5 ppm; 2H(s) 4.8 ppm; 2H(q) 4 ppm; 4H(s) 9.7 ppm; 2H(m) 3.4 to 3.7 ppm; 3H(s) 3.6 ppm; 2H(t) 2.9 ppm; 3H(s) 2.3 ppm; 2H(m) exchangeable with D$_2$O 1.4 to 1.8 ppm; 3H(t) 1.2 ppm.

Optical rotation in 1% strength solution in chloroform:

| λ (nm) | $[\alpha]^{20.5°\,C.}$ |
|---|---|
| 589 | −36.5 |
| 578 | −38.7 |
| 546 | −46.8 |
| 436 | −113 |

EXAMPLE 51

(−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine fumarate (−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine fumarate is obtained after solubilization of 4.2 g of the compound of Example 50 in 50 ml of a 0.172M ethanolic solution of fumaric acid. It is recrystallized in acetonitrile.

Yield: 92%

Melting point: 115° C.

Proton nuclear magnetic resonance spectrum (Solvent CDCl$_3$ and DMSO-d$_6$): 2H(2d split) 7.3 ppm; 1H(t) 7.1 ppm; 2H(s) 6.7 ppm; 1H(s) 5.45 ppm; 2H(m) 4.7 ppm; 2H(q) 4 ppm; 6H(m) 5.7 ppm; 3H(s) 3.6 ppm; 2H(m) 3.1 ppm; 3H(s) 2.3 ppm; 3H(t) 1.3 ppm; 1H(s exchanged D$_2$O) 7.7 ppm; 4H(s exchanged D$_2$O) 5.7 ppm.

Optical rotation in 1% strength solution in DMSO:

| λ (nm) | $[\alpha]^{20.5°\,C.}$ |
|---|---|
| 589 | −33.1 |
| 578 | −35.2 |
| 546 | −43.0 |
| 436 | −134.6 |

EXAMPLE 52

(−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine (+)-tartrate 0.2 g of the compound of Example 50 is dissolved in 3.1 ml of a 0.133M ethanolic solution of (+)-tartaric acid. After evaporation of the solvent, 0.24 g of the expected salt is obtained.

Melting point: 150° C.

Optical rotation in 1% strength solution in DMSO:

| λ (nm) | $[\alpha]^{21.5°\,C.}$ |
|---|---|
| 589 | −29.9 |
| 578 | −32.5 |
| 546 | −40.5 |
| 436 | −133.9 |

EXAMPLE 53

(−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine (−)-tartrate 0.3 g of the compound of Example 50 is dissolved in 4.6 ml of a 0.133M ethanolic solution of (−)-tartaric acid. The expected salt is isolated after filtration.

Melting point: 161°–166° C. (sublimation)

Optical rotation in 1% strength solution in DMSO:

| λ (nm) | $[\alpha]^{21.5°\ C.}$ |
|--------|------------------------|
| 589    | −32.9                  |
| 578    | −35                    |
| 546    | −42.8                  |
| 436    | −142.4                 |

EXAMPLE 54

(−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine racemic tartrate 0.45 g of the compound of Example 50 is dissolved in 6.9 ml of a 0.133M ethanolic solution of racemic tartaric acid.

The expected salt is isolated after filtration.

Melting point: 160°–170° C.

Optical rotation in 1% strength solution in DMSO:

| λ (nm) | $[\alpha]^{21.5°\ C.}$ |
|--------|------------------------|
| 589    | −31.2                  |
| 578    | −33.5                  |
| 546    | −41.1                  |
| 436    | −135.9                 |

TABLE I
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 1 |  | H | CH₃ | H | H | CH₃ | —CH₂—O— | —O— | 2 | 2 | H | H | (DMSO-d₆) (s) 1,1 ppm,t,3H; 2,3 ppm,s,3H; 2.8 to 3.2 ppm,m,2H; 3.3 to 4.7 ppm,m,11H; 4.7 ppm,s,2H; 5.4 ppm,s,1H; 6.5 ppm,s,1H; 4H exchangeable 4.9–5.7 ppm |
| 2 |  | H | CH₃ | H | H | CH₃ | —CH₂—O— | O | 2 | 2 | H | H | (CDCl₃) (b) 1,2 ppm,s,3H; 2,3 ppm,s,3H; 2,9 ppm,t,2H; 3,6 ppm,m,3H 3.4–3.7 ppm,m,2H; 3.7 ppm,s,4H; 4 ppm,m,2H, 4.7 ppm,s,2H; 5.1 ppm, s,1H; 5.9 ppm,s,2H; 6.5–6.9 ppm, m,3H; 1.5 ppm,2H exchangeable; 7.3 ppm,1H exchangeable |
| 3 |  | H | CH₃ | H | H | CH₃ | —CH₂—O— | O | 2 | 2 | H | H | (CDCl₃)(b) 1,2 ppm,t,3H; 2,3 ppm,t,3H; 2,9 ppm,t,2H; 4 ppm,m,2H; 4.7 ppm,s,2H; 5.1 ppm, s,1H; 6.5 ppm,d,1H; 6.8 ppm,d,1H; 1.5 ppm,2H exchangeable; 7.3 ppm,1H exchangeable |
| 4 | 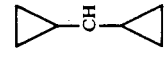 | H | 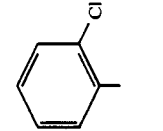 | H | H | CH₃ | —CH₂—O— | O | 2 | H | H | | |

TABLE I-continued
COMPOUNDS OF GENERAL FORMULA I

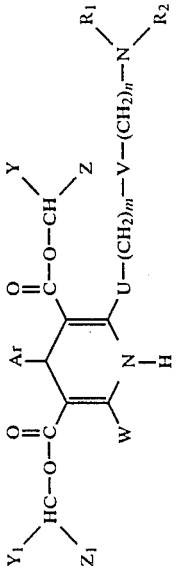

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 5 | 2-Cl-C6H4 | H | CH3 | H | H | CH3 | —CH2—O— | O | 2 | 2 | H | H | (CDCl3)(b) 1.2 ppm,t,3H; 2.3 ppm,s,3H; 3.0 ppm,t,2H; 3.6 ppm,s,3H; 3.7 ppm,t,2H; 3.9 ppm,s,4H; 4.2 ppm, m,2H; 4.7 ppm,s,2H; 5.4 ppm,s,1H; 7 14 7.6 ppm,4H; 1.7 ppm,2H exchangeable; 7.3 ppm,1H exchangeable |
| 6 | 2,3-diCl-C6H3 | H | CH3 | H | H | CH3 | —CH2—O— | O | 2 | 2 | H | H | (CDCl3)(b) 1.2 ppm,t,3H; 2.3 ppm,s,3H; 2.9 ppm,t,2H; 3.6 ppm,s,3H; 3.4-3.7 ppm,m,2H; 3.7 ppm,s,4H; 4.0 ppm,m,2H; 4.8 ppm,s,2H; 5.5 ppm,s,1H; 6.9-7.6 ppm,m,3H; 1.4-1.6 ppm,2H exchangeable; 6.9-7.6 ppm,1H exchangeable |
| 7 | 2-Cl-C6H4 | H | CH3 | H | H | CH3 | —CH2—O— | O | 2 | 2 | CH3 | CH3 | (CDCl3)(b) 1.2 ppm,t,3H; 2.3 ppm,d,6H; 2.6 ppm,t,2H; 3.4-3.8 ppm, m,9H; 4.0 ppm,m,2H; 4.7 ppm,s,2H; 5.4 ppm,s,1H; 7.3 ppm,s,5H; 6.9-7.5 ppm, m,5H; 6.9-7.5 ppm,1H exchangeable |
| 8 | 2-Cl-C6H4 | H | CH3 | H | H | CH3 | —CH2—O— | O | 2 | 2 | CH2CH=CH2 | CH2CH=CH2 | (CDCl3)(b) 1.2 ppm,t,3H; 2.3 ppm,s,3H; 2.7 ppm,t,2H; 3.1 ppm,d,4H; 3.5-3.9 ppm,m,9H; 4.0 ppm, m,2H; 4.2 ppm, s,2H; 5.0-5.5 ppm,s,1H; 5.4 ppm,s,1H; 5.5-6.5 ppm,m,2H; 6.9-7.6 ppm, m,4H; 6.9-7.6 ppm,1H |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 9 | 2-Cl-phenyl | H | CH$_3$ | H | CH(cyclopropyl)$_2$ | CH$_3$ | —CH$_2$—O— | O | 2 | 2 | H | H | (CDCl$_3$)(b) 0.0–0.9 ppm, m, 11H; 1.2 ppm, t, 3H; 2.3 ppm, s, 3H; 2.9 ppm, t, 2H; 3.4–3.7 ppm, m, 2H; 3.7 ppm, s, 4H; 4.1 ppm, m, 2H; 3.9–4.3 ppm, m, 2H; 4.8 ppm, s, 2H; 5.4 ppm, s, 1H; 6.9–7.5 ppm, m, 4H; 1.4–1.8 ppm, 2H exchangeable; 6.9–7.5 ppm, 1H exchangeable |
| 10 | 2,3-diCl-phenyl | H | CH$_3$ | H | H | CH$_3$OCH$_2$ | CH$_2$—O— | O | 2 | 2 | H | H | (CDCl$_3$)(b) 1,2 ppm, t, 3H; 3.5 ppm, s, 4H; 3,6 ppm, s, 3H; 3.7 ppm, s, 3H; 3,4–3,8 ppm, m, 2H; 4.1 ppm, q, 2H; 4.7 ppm, s, 2H; 4,8 ppm, s, 2H; 5.5 ppm, s, 1H; 7.0–7.6 ppm, m, 3H; 1,9 ppm, 1H exchangeable; 8.5 ppm, 1H exchangeable |
| 11 | 2,3-diCl-phenyl | H | CH$_3$ | H | H | CH$_3$ | CH$_2$—O— | O | 2 | 2 | CH$_2$-phenyl | CH$_3$ | (CDCl$_3$)(s) 1.1 ppm, t, 3H; 2.3 ppm, s, 3H; 3.5–4.2 ppm, m, 8H; 3.3 ppm, s, 6H; 3.6 ppm, s, 3H; 4 ppm, m, 2H; 4.7 ppm, s, 2H; 5.1 ppm, s, 2H; 5.4 ppm, s, 1H; 6.9–7.9 ppm, m, 8H; 6.9–7.9 ppm, 1H exchangeable |
| 12 | 3-Cl-phenyl | H | CH$_3$ | H | H | CH$_3$ | CH$_2$ | CH$_2$ | 2 | 3 | H | H | (CDCl$_3$)(b) 1,2 ppm, t, 1,2–1,8 ppm, m, 10H; 2,3 ppm, s, 3H; 4.1 ppm, m, 2H; 5.4 ppm, s, 1H; 6.9–7.6 ppm, m, 4H; 5.4 ppm, 2H exchangeable; 5.8 ppm, 1H exchangeable |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 13 | 2-Cl-phenyl | H | CH(cyclopropyl)₂ | H | H | CH₂ | CH₂ | CH₂ | 2 | 3 | H | H | (CDCl₃)(b) 0.0–0.9 ppm, m, 11H; 1.2–2.0 ppm, m, 10H; 2.4 ppm, s, 3H; 2.5–3.1 ppm, m, 4H; 3.7 ppm, s, 3H; 4.1–4.4 ppm, m, 2H; 5.5 ppm, s, 1H; 7.0–7.6 ppm, m, 4H; 2.2–4.0 ppm, 2H exchangeable; 6.0–6.3 ppm, 1H exchangeable |
| 14 | 2-Cl-phenyl | H | CH₃ | H | CH₃ | CH₃ | CH₂ | CH₂ | 1 | 2 | H | H | (CDCl₃)(b) 1,2 ppm, t, 3H; 1,1–1,9 ppm, m, 4H; 2,3 ppm, s, 3H; 2.3–3.0 ppm, m, 4H; 3,6 ppm, s, 3H; 4,1 ppm, m, 2H; 5.4 ppm, s, 1H; 6.9–7.6 ppm, m, 4H; 1.1–1,9 ppm, 2H exchangeable; 6,5 ppm, 1H exchangeable |
| 15 | pentafluorophenyl | H | CH₃ | H | CH₃ | CH₃ | —CH₂—O— | O | 2 | 2 | H | H | (CDCl₃)(b) 1,2 ppm, t, 6H; 2.35 ppm, s, 3H; 2,9 ppm, m, 2H; 3.65 ppm, m, 2H; 3.7 ppm, s, 2H; 4.1 ppm, m, 4H; 4.75 ppm, s, 2H; 5.5 ppm, s, 1H; 1.8 ppm, 2H exchangeable; 7.7 ppm, 1H exchangeable |
| 16 | pentafluorophenyl | H | CH₃ | H | CH₃ | CH₃ | —CH₂—O— | —O— | 2 | 2 | H | C₃H₇ | (DMSO-d₆)(s) 0.9 ppm, t, 3H; 1.1 ppm, t, 6H; 1.6 ppm, m, 2H; 2.3 ppm, s, 3H; 2.6–3.3 ppm, m, 4H; 3.6 ppm, m, 6H; 3.9 ppm, q, 4H; 4.6 ppm, s, 2H; 5.4 ppm, s, 1H; 7.9 and 8.8 ppm, 4H exchangeable |

TABLE I-continued
COMPOUNDS OF GENERAL FORMULA I

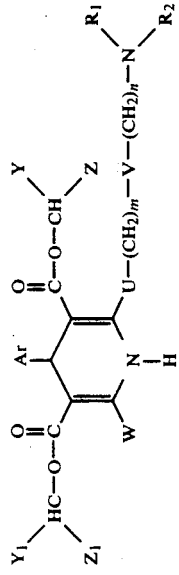

| EX. | Ar | Y | Z | Y1 | Z1 | W | U | V | m | n | R1 | R2 | NMR (SOLVENT)<br>(b): base; (s): salt |
|---|---|---|---|---|---|---|---|---|---|---|---|---|---|
| 17 | 2-CF$_3$-phenyl | H | CH$_3$ | H | H | CH$_3$ | —CH$_2$—O | —O— | 2 | 2 | H | H | (CDCl$_3$)(b)<br>1.15 ppm,t,3H; 2.35 ppm,<br>s,3H; 2.95 ppm,t,2H; 3.6<br>ppm,t,2H; 3.65 ppm,s,4H;<br>3.75 ppm,s,3H; 4.15<br>ppm, q,2H; 4.85 ppm,s,2H;<br>5.7 ppm,s,1H; 7.0–8.0 ppm,<br>m,4H; 1.8 ppm,2H exchange-<br>able; 7.0–8.0 ppm,1H<br>exchangeable |
| 18 | 3-Cl-phenyl | H | CH$_3$ | H | H | CH$_3$ | CH$_2$—O | —O— | 2 | 2 | H | H | (DMSO—d$_6$)(s)<br>1.2 ppm,t,3H; 2.3 ppm,s,3H;<br>3 ppm,m,2H; 3.3–4,5 ppm,<br>m,13H; 4.7 ppm,s,2H; 4.9<br>ppm,s,1H; 6.8 ppm,m,6H;<br>7.2 ppm,s,4H; 8.6 ppm,1H<br>exchangeable |
| 19 | pentafluorophenyl | H | H | H | H | CH$_3$ | CH$_2$—O | —O— | 2 | 2 | H | H | (CDCl$_3$)(b)<br>2,3 ppm,s,3H; 2.9 ppm,<br>m,2H; 3.55 ppm,m,2H; 3.6<br>ppm and 3.7 ppm,2s,10H; 4,7<br>ppm,s,2H; 5.5 ppm,s,1H; 2,2<br>ppm,2H exchangeable 7.7<br>ppm, 1H exchangeable |
| 20 | pentafluorophenyl | H | H | H | CH$_3$ | CH$_3$ | CH$_2$—O | —O— | 2 | 2 | H | H | (CDCl$_3$)(b)<br>1.2 ppm,t,3H; 2.35 ppm,<br>s,3H; 2.5–3.3 ppm,m,2H;<br>3.55 ppm,m,2H; 3.6 ppm,<br>s,3H; 3.7 ppm,s,4H; 4.05<br>ppm,q,2H; 4.7 ppm,s,2H; 5.5<br>ppm,s,1H; 1.5–2.3 ppm,2H<br>exchangeable 7.6 ppm,1H<br>exchangeable |

TABLE I-continued
COMPOUNDS OF GENERAL FORMULA I

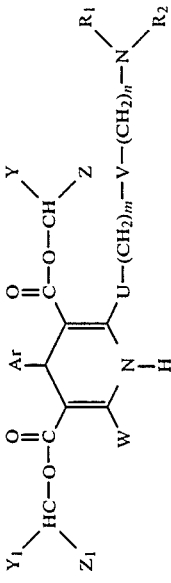

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 21 | pentafluorophenyl | H | CH₃ | H | H | CH₃ | CH₂—O | —O— | 2 | 2 | H | COCF₂ | (CDCl₃ + DMSO)(b) 1.2 ppm,t,3H; 2.35 ppm, s,3H; 3.3–3.9 ppm, m,4H; 3.6 ppm,s,3H; 3.7 ppm,s,4H; 4.1 ppm,q,2H; 4.75 ppm,s,2H; 5.5 ppm,s,1H; 7.8 ppm, 1H exchangeable 8.5 ppm, 1H exchangeable |
| 22 | 2-SCH₃, 6-OCH₃ phenyl | H | CH₃ | H | H | CH₃ | CH₂—O | —O— | 2 | 2 | H | H | (DMSO—d₆)(s) 1.2 ppm,t,3H; 2.3 ppm,s,3H; 2.4 ppm,s,3H; 3.0 ppm,t,2H; 3.3–3.7 ppm, m,9H; 3.8 ppm, s,3H; 4.1 ppm,q,2H; 4.6 ppm,m,2H; 5.3 ppm,s,2H; 6.6 ppm,s,2H; 6.8–7.3 ppm, m,3H; 7.7 and 8.7 ppm,5H exchangeable |
| 23 | pentafluorophenyl | H | 4-NO₂-phenyl | H | H | CH₃ | CH₂—O | —O— | 2 | 2 | H | H | (CDCl₃)(b) 2.35 ppm,s,4H; 2.95 ppm, m,2H; 3.6 ppm,m,2H; 3.65 ppm,s,3H; 3.7 ppm,s,4H 4.8 ppm,s,2H; 5.2 ppm,s,2H; 5.5 ppm,s,1H; 7.5 ppm, d,2H; 8.3 ppm,d,2H; 2.0 ppm,2H exchangeable 7.9 ppm,1H exchangeable |
| 24 | pentafluorophenyl | H | CH₃ | H | H | CH₃ | CH₂—O | —O— | 3 | 3 | H | H | (CDCl₃)(b) 1.1 ppm,t,3H; 1.9 ppm,m,4H; 2.3 ppm,s,3H; 2.8 ppm,m,2H; 3.5 ppm,m,6H; 3.6 ppm,s,3H; 4.1 ppm,q,2H; 4.6 ppm,s,2H; 5.5 ppm, s,1H; 7.6 ppm,1H exchangeable |

TABLE I-continued
COMPOUNDS OF GENERAL FORMULA I

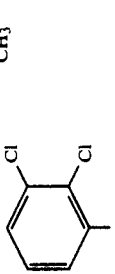

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 25 | 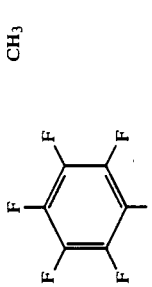 2,3-diCl-phenyl | CH₃ | CH₃ | H | H | CH₃ | CH₂—O | —O— | 2 | 2 | H | H | (CDCl₃)(b) 1.0 and 1.25 ppm,4d,6H; 2.3 ppm,s,3H; 3.0 ppm,m,2H; 3.5 ppm,m,2H; 3.6 ppm,s,3H; 3.7 ppm,s,4H; 4.8 ppm,s,2H; 4.9 ppm,m,1H; 5.5 ppm,s,1H; 7.0–7.8 ppm,m, 3H + 1 exchangeable 1.7 ppm, 1H exchangeable |
| 26 | 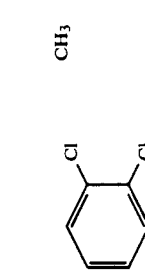 pentafluorophenyl | CH₃ | CH₃ | H | H | CH₃ | CH₂—O | —O— | 2 | 2 | H | H | (CDCl₃)(b) 1.0 ppm,d,3H; 1,2 ppm, d,3H; 2,3 ppm,s,3H; 2.6–3,3 ppm,m,2H; 3.55 ppm,m,2H; 3.6 ppm,s,3H; 3.7 ppm,s,4H; 4.7 ppm,s,2H; 5.0 ppm, m 1H; 5.5 ppm,s,1H; 1.5–2.0 ppm,2H exchangeable; 7.7 ppm,1H exchangeable |
| 27 | 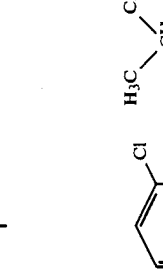 2,3-diCl-phenyl | CH₃ | H | H | H | CH₃ | CH₂—O | —O— | 3 | 3 | H | H | (CDCl₃)(b) 1.2 ppm,t,3H; 1.9 ppm,m,4H; 2,4 ppm,s,3H; 2.8 ppm,m,2H; 3,4–3,8 ppm,m,6H; 3.6 ppm,s,3H; 4.1 ppm,q,2H; 4.7 ppm,s,2H; 5.5 ppm,s,1H; 6,9–7,6 ppm, m,3H; 2,2 ppm,2H exchangeable; 6.9–7.6 ppm,1H exchangeable |
| 28 | 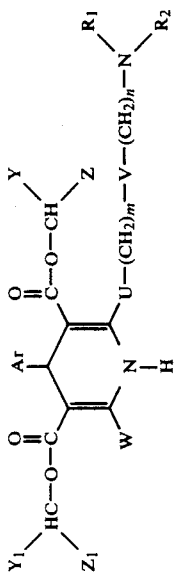 2,3-diCl-phenyl | H₃C—CH(CH₃)— | H | H | H | CH₃ | CH₂—O | —O— | 2 | 2 | H | H | (DMSO—d₆)(s) 0,5–1 ppm,m,6H; 1–2 ppm, m,1H; 2,3 ppm,s,3H; 2.8–3.2 ppm,m,2H; 3.2–4.0 ppm, m,11H; 4.7 ppm,s,2H; 5.4 ppm,s,1H; 6,5 ppm,s,2H; 7.5 exchangeable 8.5–9.0 ppm, 1H exchangeable |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 29 | 2,3-diCl-phenyl | H | CH(cyclopropyl)₂ type group | H | H | CH₃ | CH₂—O | —O— | 2 | 2 | H | H | (CDCl₃)(b) 0–1.4 ppm,m,11H; 2.3 ppm,s,3H; 2.9 ppm,m,2H; 3.5 ppm,m,2H; 3.6 ppm,s,3H; 3.7 ppm,s,4H; 4.5 ppm,m,2H; 4.8 ppm,s,2H; 5.4–5.8 ppm,m,3H; 6.8–7.7 ppm,m,3H; 1.2–2.0 ppm,2H exchangeable; 6.8–7.7 ppm, 1H exchangeable |
| 30 | 2-CF₃-6-SCH₃-phenyl | H | CH₃ | H | H | CH₃ | CH₂—O | —O— | 2 | 3 | H | H | (DMSO—d₆)(s) 1.15 ppm,t,3H; 1.5–2.0 ppm,m,4H; 2.3 ppm,s,6H; 2.9 ppm,t,2H; 3.2–3.7 ppm,m,6H; 3.6 ppm,s,3H; 4.1 ppm,q,2H; 4.5 ppm,s, 2H; 5.9 ppm,s,1H; 6,6 ppm,s,2H; 7.5–7.8 ppm,m, 3H; 6.6–7.4 ppm,4H exchangeable 8.8 ppm,1H exchangeable |
| 31 | 2,4,6-triCl-phenyl | H | CH₃ | H | H | CH₃ | CH₂—O | —O— | 2 | 2 | H | H | (DMSO—d₆)(s) 1.1 ppm,t,3H; 2.3 ppm,s,3H; 2.7–3.2 ppm,m,2H; 3.4–3.7 ppm,m + s,6H + 3H; 3.8–4.2 ppm,q,2H; 4.6 ppm,s,2H; 6.5 ppm,q,2H; 4.7 –5.7 ppm,1H +5H exchangeable 6.5 ppm,s,2H; 7.3 ppm,d,1H; 7.6 ppm,d,1H |
| 32 | 2,3,5-triCl-phenyl | H | CH₃ | H | H | CH₃ | CH₂—O | —O— | 3 | 3 | H | H | (CDCl₃)(b) 1.1 ppm,t,3H; 2.3 ppm,s,3H; 2.9 ppm,m,2H; 3,65 ppm,s,3H; 3.7 ppm,s,4H; 4.1 ppm,q,2H; 4.7 ppm,s,2H; 6.0 ppm,s, 1H; |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 33 | 2,3-Cl₂-C₆H₃ | H | (CH₂)₂CH(cyclopropyl)₂ | H | H | CH₃ | CH₂—O | —O— | 2 | 2 | H | H | 7.1–7.3 ppm,m,2H; 1.4 ppm, 2H exchangeable 7.6 ppm, 1H exchangeable (CDCl₃)(b) 0.0–0.8 ppm,m,10H; 1.0–2.2 ppm,m,5H and 2H exchangeable; 2,3 ppm,s,3H; 2.9 ppm,m,2H; 3.5 ppm,m,2H; 3.6 ppm,s,3H; 3.7 ppm,s,4H; 4.1 ppm,m,2H; 4.8 ppm, s,2H; 5.5 ppm,s,1H; 7.0–7.5 ppm,m, 3H + 1H exchangeable |
| 34 | 2,3,4,5-F₄-C₆H | CH₃ | H | H | H | CH₃ | CH₂—O | —O— | 2 | 2 | H | C₃H₇ | (CDCl₃)(b) 0.9 ppm,t,3H; 1.2 ppm,t,3H; 1.4–2.0 ppm,m, 3H + 1H exchangeable 2.3 ppm,s,3H; 2.4–3.1 ppm,m,4H; 3.6 ppm, s,3H; 3.4–3.8 ppm,m, 6H; 4.1 ppm,q,2H; 4.75 ppm,s,2H; 5.5 ppm,s,1H; 7.7 ppm,1H exchangeable |
| 35 | 2-CF₃-3-Cl-C₆H₃ | —CH₃ | —CH₃ | H | H | CH₃ | CH₂—O | —O— | 2 | 2 | H | H | (CDCl₃)(b) 0.9 ppm,d,3H; 1.3 ppm,d,3H; 1.5–2.2 ppm, m,2H exchangeable 2.3 ppm,s,3H; 2.9 ppm,m,2H; 3.6 ppm,s,3H; 3.3–3.9 ppm, m,6H; 4.7 ppm,s,2H; 5.0 ppm,m,1H; 5.5 ppm,s,1H; 6.9–8.0 ppm,m,3H + 1H exchangeable |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 36 | 2-Cl, 3-CF₃ phenyl | H | (CH₂)₂CH(cyclopropyl)₂ | H | H | CH₃ | CH₂—O | —O— | 2 | 2 | H | H | (CDCl₃)(b) 0.0–0.8 ppm,m,10H; 1.0–2.0 ppm,m,7H + 2H exchangeable; 2.3 ppm,s,3H; 2.7–3.2 ppm,m,2H; 3.6 ppm,s,3H; 3.3–4.2 ppm,m,8H; 4.8 ppm,s,2H; 5.6 ppm,s,1H; 7.0–8.0 ppm,m,4H + 1H exchangeable |
| 37 | 2-Cl, 3-CF₃ phenyl | H | CH(cyclopropyl)CH=CH(cyclopropyl) | H | H | CH₃ | CH₂—O | —O— | 2 | 2 | H | H | (CDCl₃)(b) 0.0–1.0 ppm,m,3H + 2H exchangeable; 2.3 ppm,s,3H; 2.9 ppm,m,2H; 3.6 ppm,s,3H; 3.3–4.0 ppm,m,6H; 4.5 ppm,m,3H; 4.8 ppm,s,2H; 5.0–6.0 ppm, m,2H; 5.6 ppm,s,1H; 6.9–7.0 ppm,m,3H + 1H exchangeable |
| 38 | 2-Cl, 3-CF₃ phenyl | H | CH(CH₃)₂ | H | H | CH₃ | CH₂—O | —O— | 2 | 2 | H | H | (CDCl₃)(b) 0.45 ppm,d,3H; 0.55 ppm,d,3H; 1.3–2.2 ppm,m,1H + 2H exchangeable 2.3 ppm,s,3H; 2.9 ppm,m,2H; 3.6 ppm,s,3H; 3.4–4.0 ppm,m,8H; 4.8 ppm,s,2H; 5.5 ppm,s,1H; 7.0–7.8 ppm,m,3H + 1H exchangeable |
| 39 | 2,3-diCl phenyl | H | C(=CH₂)CH₃ | H | H | CH₃ | CH₂—O | —O— | 2 | 2 | H | H | (CDCl₃)(b) 1.6 ppm,s,3H; 1.4–1.7 ppm, 2H exchangeable; 2.3 ppm,s,3H; 2.6 to 3.3 ppm, m,2H; 3.6 ppm,s,3H; 3.3–3.8 ppm,m,6H; 4.5 ppm,s,2H; |

TABLE I-continued
COMPOUNDS OF GENERAL FORMULA I

| EX. | Ar | Y | Z | Y1 | Z1 | W | U | V | m | n | R1 | R2 | NMR (SOLVENT) (b): base; (s): salt |
|---|---|---|---|---|---|---|---|---|---|---|---|---|---|
| 40 | 2,3-dichlorophenyl | H | CH₃ | H | H | CH₃ | (CH₂)₂—O | —O— | 2 | 2 | H | H | 4.7–5.0 ppm,4H; 5.5 ppm, s,1H; 7.0–7.6 ppm,m,3H + 1H exchangeable<br><br>(CDCl₃)(b)<br>1.2 ppm,t,3H;<br>2,3 ppm,s,3H; 2,6 ppm,t,2H;<br>2,9 ppm,m,2H; 3,4–4.0 ppm,m,8H; 3,6 ppm,s,3H;<br>3,9 ppm,q,2H; 5,0 ppm,m, 3H exchangeable, 5.4 ppm,s, 1H; 6.9–7.7 ppm,m,3H |

PHARMACOLOGICAL STUDY

EXAMPLE 55

Determination of the Vitro Activity in Rat Aorta Stimulated by Potassium Ions

This trial was carried out using isolated organs removed from male Wistar rats weighing 300 to 400 g, kept under a water diet 18 hours before sacrificing.

After quickly sacrificing the animal, the aorta (at the level of the arch of the aorta) is removed and dissected into 2 mm-long rings; the endothelium is removed mechanically. After an equilibration period of 1 hour in a physiological solution consisting of (mM): NaCl 112, KCl 5, $KH_2PO_4$ 1, $MgSO_4$ 1.2, $CaCl_2$ 2.5, $NaHCO_3$ 25 and glucose 11.5, the preparations are stimulated with a potassium-rich solution. The latter consists of (mM):NaCl 37, KCl 80, $KH_2PO_4$ 1, $MgSO_4$ 1.2, $CaCl_2$ 2.5, $NaHCO_3$ 25 and glucose 11.5. This solution has a pH of 7.4 at 37° C.

After 15 minutes of stabilization, the compounds to be tested are then added (sample volume 0.2 ml) at cumulative doses at 60 minutes intervals. From the relaxation values obtained, it is possible to construct a doseresponse curve, leading to the calculation of an $IC_{50}$ value (expressed in M).

The results of this study are given in Table II below.

TABLE II

| COMPOUNDS | $IC_{50}(M)$ |
| --- | --- |
| EXAMPLE 1 | $2.5 \times 10^{-8}$ |
| EXAMPLE 2 | $3.0 \times 10^{-8}$ |
| EXAMPLE 3 | $1.0 \times 10^{-6}$ |
| EXAMPLE 4 | $3.0 \times 10^{-7}$ |
| EXAMPLE 5 | $6.5 \times 10^{-8}$ |
| EXAMPLE 6 | $5.0 \times 10^{-9}$ |
| EXAMPLE 7 | $4.0 \times 10^{-9}$ |
| EXAMPLE 8 | $6.5 \times 10^{-9}$ |
| EXAMPLE 9 | $3.0 \times 10^{-6}$ |
| EXAMPLE 10 | $9.0 \times 10^{-8}$ |
| EXAMPLE 11 | $2.5 \times 10^{-7}$ |
| EXAMPLE 12 | $2.5 \times 10^{-8}$ |
| EXAMPLE 13 | $3.0 \times 10^{-7}$ |
| EXAMPLE 14 | $4.0 \times 10^{-8}$ |
| EXAMPLE 15 | $1.2 \times 10^{-7}$ |
| EXAMPLE 16 | $6.1 \times 10^{-8}$ |
| EXAMPLE 17 | $7.6 \times 10^{-9}$ |
| EXAMPLE 18 | $4.7 \times 10^{-9}$ |
| EXAMPLE 19 | $4.9 \times 10^{-9}$ |
| EXAMPLE 20 | $2.6 \times 10^{-8}$ |
| EXAMPLE 21 | $6.8 \times 10^{-8}$ |
| EXAMPLE 22 | $2.0 \times 10^{-8}$ |
| EXAMPLE 23 | $2.0 \times 10^{-7}$ |
| EXAMPLE 24 | $8.2 \times 10^{-10}$ |
| EXAMPLE 25 | $1.3 \times 10^{-8}$ |
| EXAMPLE 26 | $3.1 \times 10^{-7}$ |
| EXAMPLE 27 | $4.4 \times 10^{-9}$ |
| EXAMPLE 28 | $9.3 \times 10^{-9}$ |
| EXAMPLE 29 | $7.5 \times 10^{-8}$ |
| EXAMPLE 30 | $2.5 \times 10^{-8}$ |
| EXAMPLE 31 | $1.7 \times 10^{-7}$ |
| EXAMPLE 32 | $3.2 \times 10^{-8}$ |
| EXAMPLE 33 | $7.7 \times 10^{-8}$ |
| EXAMPLE 34 | $1.1 \times 10^{-9}$ |
| EXAMPLE 35 | $2.1 \times 10^{-8}$ |
| EXAMPLE 36 | $4.7 \times 10^{-7}$ |
| EXAMPLE 37 | $3.5 \times 10^{-7}$ |
| EXAMPLE 38 | $6.1 \times 10^{-8}$ |
| EXAMPLE 39 | $8.0 \times 10^{-8}$ |

EXAMPLE 56

Study in Conscious Dogs with Renal Hypertension

Mongol dogs weighing 20 to 25 kg are used. A Silastic ® catheter, inserted under anesthesia at the level of the abdominal aorta, left in position permanently, enables the arterial pressure to be determined subsequently in the conscious animal.

Arterial hypertension is induced by a second operation, under anesthesia, consisting in constricting the left renal artery with a clip, decreasing the flow rate therein by approximately 70%, the left kidney is also covered with a latex capsule in order to restrict circulatory compensations; the contralateral kidney is left in position.

The systolic, diastolic and mean arterial pressures are determined with a Statham ® $P_{23}$ pressure sensor attached to the Silastic ® catheter and connected to a Gould ® "pressure-processor". The compounds are tested in animals which became hypertensive in the conscious state at least one week after the second operation. The arterial pressure is continuously recorded up to 7 hours after the treatment and then at 24 hours.

The compounds to be tested are administered by the digestive route through gastric tubing, in the form of a solution which may be aqueous, aqueous/alcoholic and the like, depending on the solubility of the products.

The doses administered are expressed in mg base per body weight kg.

The compounds of the invention were compared with a 1,4-dihydropyridine derivative reference compound, amlodipin. The results of this study are given in Table III.

As can be seen from these two tables, the compounds of the present invention have an activity comparable to amlodipine, but the period of action thereof is much longer.

TABLE III

| | | | MEAN ARTERIAL PRESSURE | | |
| --- | --- | --- | --- | --- | --- |
| | | | AFTER TREATMENT | | |
| | DOSE | CONTROL | $\Delta$ mm Hg | | |
| COMPOUNDS | mg/kg | mm Hg | 4 h | 7 h | 24 h |
| EXAMPLE 1 | 0.5 | 133 | −21 | −22 | −15 |
| | 1.0 | 135 | −45 | −47 | −46 |
| EXAMPLE 5 | 0.5 | 131 | −32 | −25 | n.d. |
| | 1.0 | 128 | −48 | −39 | −10 |
| EXAMPLE 6 | 0.5 | 136 | −20 | −29 | −11 |
| | 1.0 | 129 | −40 | −44 | −49 |
| EXAMPLE 7 | 0.5 | 125 | −7 | −3 | 0 |
| EXAMPLE 12 | 2.0 | 120 | −22 | −32 | n.d. |
| AMLODIPINE | 0.5 | 133 | −28 | −20 | −10 |
| | 1.0 | 146 | −45 | −39 | −29 | n.d.: not determined

EXAMPLE 57

Short-term Studies in Conscious Spontaneous Hypertensive Rats (SHR)

Male spontaneous hypertensive rats weighing 270 to 320 g, aged 16 to 24 weeks, are anesthetized with ether. A polyethylene catheter is introduced into the femoral artery and moved forward to the level of the tail. The pressure in the femoral artery is recorded with a Statham ® $P_{23}$ sensor, on a Gould ® 2400 recorder. The animals are treated at least one hour after the operation. The compounds are administered orally, in the dissolved form. The doses administered are expressed in mg/kg of base. The compounds of the invention were compared with amlodipine and with another 1,4-dihydropyridine derivative reference compound, nifedipine.

The results of this study are reported in Table IV. As in the previous example, the compounds of the present invention are distinguishable from the reference compounds by the strength and the duration of their antihypertensive activity.

TABLE IV

| COMPOUNDS | DOSE mg/kg | CONTROL mm Hg | SYSTOLIC ARTERIAL PRESSURE AFTER TREATMENT Δ mm Hg | | |
|---|---|---|---|---|---|
| | | | 4 h | 6 h | 24 h |
| EXAMPLE 1 | 1 | 208 | −44 | −54 | −47 |
|  | 3 | 212 | −79 | −78 | −71 |
| EXAMPLE 2 | 3 | 200 | −13 | −16 | n.d. |
| EXAMPLE 5 | 3 | 219 | −49 | −49 | −22 |
| EXAMPLE 6 | 1 | 205 | −14 | −17 | −17 |
|  | 3 | 194 | −52 | −55 | −36 |
| EXAMPLE 7 | 3 | 207 | −22 | −16 | −8 |
| EXAMPLE 8 | 3 | 198 | −21 | −19 | n.d. |
| EXAMPLE 12 | 3 | 211 | −23 | −30 | −21 |
| AMLODIPINE | 3 | 210 | −47 | −46 | −13 |
| NIFEDIPINE | 3 | 213 | −19 | −25 | n d. | n.d.: not determined

EXAMPLE 58

Long-term Studies in Conscious Spontaneous Hypertensive rats (SHR)

Male rats weighing 280 to 300 g, aged 16 weeks, are used in this study. The systolic arterial pressure is determined with a Rhema multichannel 8,000 ® apparatus, according to the indirect method, at the tail of the animal. The compounds to be tested are administered orally, in a single daily dose.

Determinations of arterial pressure are carried out each day just before the treatment. Amlodipine was also studied under the same conditions. The results of this study are reported in Table V below. The results show that, at equal doses, the products of the present invention have a higher efficiency than amlodipine.

TABLE V

| COMPOUND | DOSE mg/kg/d | CONTROL mm Hg | SYSTOLIC ARTERIAL PRESSURE Δ(mm Hg) 24 h AFTER THE LAST ADMINISTRATION OF THE PRODUCTS | | | | |
|---|---|---|---|---|---|---|---|
| | | | $D_1^*$ | $D_2^*$ | $D_3^*$ | $D_4^*$ | $D_7^*$ |
| EXAMPLE 1 | 1 | 216 | −52 | −51 | −49 | −44 | −46 |
| EXAMPLE 6 | 1 | 214 | −22 | −18 | n.d. | −17 | −31 |
| AMLODIPINE | 1 | 200 | −9 | −8 | −14 | −14 | −9 |

*D = days

EXAMPLE 59

Affinity for the Dihydropyridine Binding Site

Study of the displacement by (−)-2-{[2-(2-aminoethoxy)ethoxy]methyl}-4-(2,3-dichlorophenyl)-3-ethoxycarbonyl-5-methoxycarbonyl-6-methyl-1,4-dihydropyridine and by its racemate of tritiated PN 200-110 bound specifically to the dihydropyridine site associated with the calcium slow channel enabled it to be demonstrated that the compound of Example 50 exhibits an affinity for these sites which is 30 times as great as its racemate.

This study was carried out on microsomal membrane preparations prepared from skeletal muscle of rat (Wistar) hind limbs.

The rats are killed by decapitation. The skeletal muscles are removed and washed in buffer I (20 mM MOPS/KOH pH 7.4, 0.3M sucrose, 1 mM EDTA, 0.1 mM iodoacetamide, 1 μM pepstatin A, 1 mg/l leupeptin and 0.1 μM PMSF). The muscles are then mechanically fragmented, taken up in 4 volumes of buffer I per gramme of tissue and homogenized.

The homogenate is then centrifuged for 10 minutes at 3,200 g, the pellets are removed and the supernatants are then centrifuged for 20 minutes at 15,000 g, and the supernatants are stirred for 15 minutes at 4° C. in buffer I containing 0.6M final KCl and then centrifgued for 45 minutes at 70,000 g.

The pellets are taken up in buffer I and homogenized in a Potter. The homogenates are centrifuged at 100,000 g for 45 minutes and the pellets thereby obtained correspond to the microsomal fraction used for the studies of binding and displacement.

The activity of the product is assessed by the displacement of [$^3$H]-PN 200-110, bound specifically to its receptor associated with the calcium slow channel, by increasing concentrations of the test products. The value obtained (K0.5) for each of the products, which represents the concentration of the product displacing 50% of the [$^3$H]-PN 200-110, permits calculation of a true dissociation constant ($K_I$):

$$K\,0.5 = K_I \times \frac{1 + [L^*]}{Kd}$$

where [L*] is the concentration of free [$^3$H]-PN 200-110 and Kd the dissociation constant at equilibrium of the [$^3$H]-PN 200-110 complex, determined by direct binding.

The $K_I$ values of the two products are recorded in Table VI

TABLE VI

| COMPOUND | $K_I$ EXPRESSED IN nM |
|---|---|
| EXAMPLE 50 | 0.28 ± 0.15 |
| EXAMPLE 6 | 8.2 ± 1.7 |

EXAMPLE 60

Study on Isolated Rabbit Mesenteric Artery Contracted with Calcium

This test is performed on organs removed from male New Zealand rabbits weighing 2.5 to 3 kg, subjected to a water regimen for 18 hours before sacrifice.

After the animal is rapidly sacrificed, the mesenteric artery is removed and dissected into rings 2 mm long; the endothelium is removed mechanically.

After a stabilization period of 90 minutes, the preparations are subjected to a depolarizing medium (35 mM KCl) without calcium (0.1 mM EGTA) for 15 minutes.

A control series is prepared by adding cumulative doses of calcium to the bath every 6 minutes until a maximum of effect is produced. The preparations are then rinsed for a period of 15 minutes and the product is incubated for one hour before renewal of the calcium series.

A single concentration of the product is tested per organ.

The responses obtained in the presence of product are expressed as a percentage of the maximal value of the control series.

The pD'2 value is calculated according to the method of Van Rossum (1963).

The pD'2 values of the compound of the invention and its racemate appear in Table VII These data show the very marked superiority (more than double) of the compound of example 50 compared with its racemate, in preventing a calcium-induced vascular contraction.

TABLE VII

| COMPOUND | pD'2 |
|---|---|
| EXAMPLE 50 | 7.97 |
| EXAMPLE 6 | 7.64 |

EXAMPLE 61

Study in Unanesthetized Spontaneously Hypertensive Rats (SHR)

SHR male rats weighing 280 to 350 g and aged from 18 to 24 weeks are anaesthetized with imalgene ® (150 mg/kg i.p.). Two polyethylene catheters are introduced, one into the abdominal aorta for the recording of hemodynamic parameters and the other into the jugular vein for the administration of the products. The catheters are taken through to neck level. The animals are used at least 48 hours after surgical intervention.

The systolic and diastolic abdominal bood pressures are recorded by means of a Statham P23XL transducer on a Gould ES 1000 recorder. The products are administered intravenously in a volume of 0.5 ml/kg. The doses administered of the test compounds are expressed in mg/kg of base. The blood pressure is recorded in continuous fashion up to 6 hours after the treatment.

The changes in systolic blood pressure after treatment are recorded in Table VIII.

The compound of example 50 is distinguished from its racemate by its activity, which is more potent and sustained even better over a period of time, this constituting a considerable advantage in therapy. In effect, for the same dose six hours after treatment, the activity of the compound of the invention is approximately 4 times as great as that of its racemate.

TABLE VIII

| COMPOUND | DOSE (mg/kg) | Systolic blood pressure changes ($\Delta$mmHg) after treatment | | |
|---|---|---|---|---|
| | | 1H 30 min | 3H | 6H |
| EXAMPLE 50 | 0.1 | −16 ± 2 | −18 ± 2 | −21 ± 5 |
| EXAMPLE 6 | 0.1 | −11 ± 3 | −5 ± 3 | −5 ± 2 |

PHARMACEUTICAL PREPARATION

EXAMPLE 62

Capsules containing a 2 mg dose of (4R,S)-2-{[2-(2-aminoethoxy)ethoxy]methyl}-3-ethoxycarbonyl-5-methoxycarbonyl-6-methyl-4-pentafluorophenyl-1,4-dihydropyridine hemifumarate (A.E.P.M.D.P.)

A.E.P.M.D.P. .... 2 mg

Corn starch ... 15 mg
Lactose ... 25 mg
Talcum ... 5 mg

EXAMPLE 63

Tablets containing a 1 mg dose of (−)-2-{[2-(2-aminoethoxy)ethoxy]methyl}-4-(2,3-dichlorophenyl)-3-ethoxycarbonyl-5-methoxycarbonyl-6-methyl-1,4-dihydropyridine (A.D.E.M.M.D.P.)

A.D.E.M.M.D.P. .... 1 mg
Starch sucrose ... 64 mg
Cellulose excipient ... 25 mg
Alginic acid ... 10 mg
per tablet of theoretical weight 100.00 mg.

We claim:

1. A process for preparing (−)-2-{[2-(2-Aminoethoxy)ethoxy]methyl}-4-(2,3-dichlorophenyl)-3-ethoxycarbonyl-5-methoxycarbonyl-6-methyl-1,4-dihydropyridine, the compound of formula XXIV:

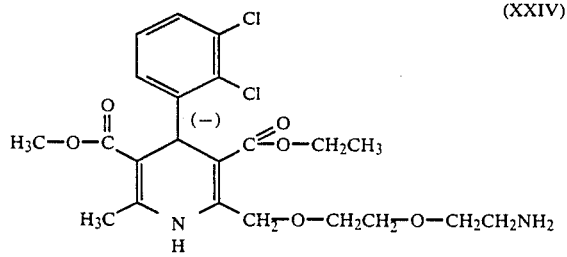

wherein 2-[2-(2-chloroethoxy)ethoxy]ethanol is condensed with potassium phthalimide, in dimethylformamide in the heated state, to form 2-[2-(2-phthalimidoethoxy)ethoxy]ethanol, the compound of formula XIV:

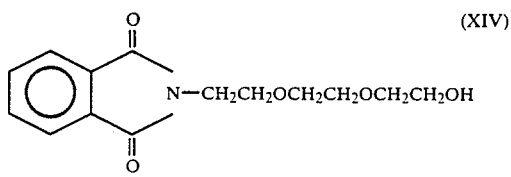

which is converted by means of Jones reagent to 2-[2-(2-phthalimidoethoxy)ethoxy] acetic acid, the compound of formula XV

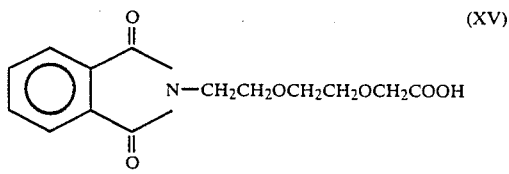

which is treated with carbonyldiimidazole and Meldrum's acid in the presence of pyridine in methylene chloride to obtain the compound of formula XVI:

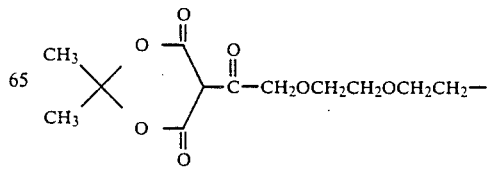

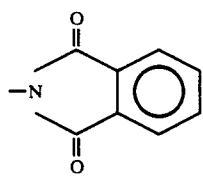

which is then reacted with (R)-2-phenyl-2-methoxyethanol, the compound of formula XVII

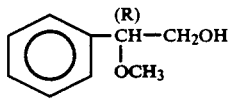
(XVII)

to obtain the β-keto ester of formula XVIII

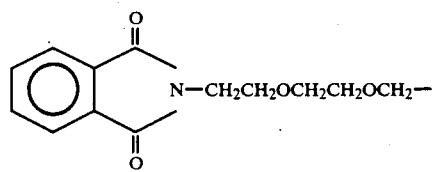
(XVIII)

which is condensed in the presence of ammonium formate in ethanol with a benzylidene compound of formula XIX

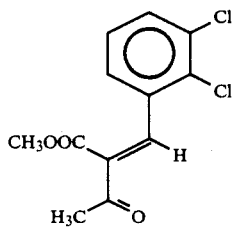
(XIX)

to obtain (4R,4′R/4S,4′R)-4-(2,3-dichlorophenyl)-5-methoxycarbonyl-3-(2-methoxy-2-phenylethoxycarbonyl)-6-methyl-2-{[2-(2-phthalimidoethoxy)ethoxy]methyl}-1,4-dihydropyridine, the compound of formula XX

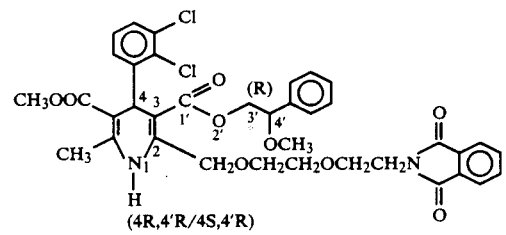
(XX)

and then: either: this compound is subjected to the action of aqueous sodium bicarbonate solution to obtain (4R,4′R/4S,4′R)-2-[{2-[2-(2-carboxyphenylcarboxamido)ethoxy]ethoxy}methyl]-4-(2,3-dichlorophenyl)-5-methoxycarbonyl-3-(2-methoxy-2-phenylethoxycarbonyl)-6-methyl-1,4-dihydropyridine, the compound of formula XXI:

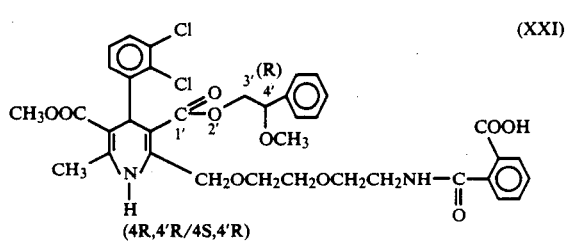
(XXI)

which is treated after separation by HPLC in the heated state with a mixture of glyme and sodium ethylate to obtain a mixture containing (−)-2-[{2-[2-(2-carboxyphenylcarboxamido)ethoxy]ethoxy}-methyl]-4-(2,3-dichlorophenyl)-3-ethoxycarbonyl-5-methoxycarbonyl-6-methyl-1,4-dihydropyridine, the compound of formula XXII:

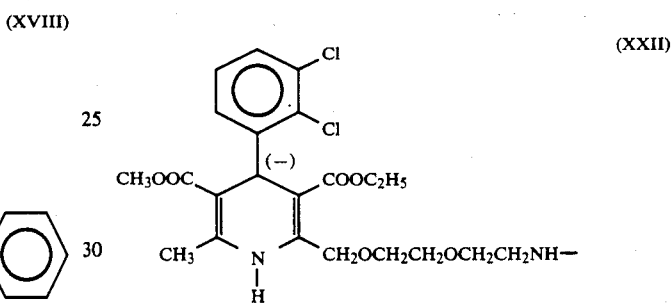
(XXII)

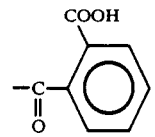

and its homolog substituted at the 5-position with an ethoxycarbonyl radical, or: the compound of formula XX is separated by chromatography on a silica column, using a mixture of methylene chloride and ethyl acetate (95:5 V/V) as eluant, to obtain the less polar isomer of 4-(2,3-dichlorophenyl)-5-methoxycarbonyl-3-(2-methoxy-2-phenylethoxycarbonyl)-6-methyl-2-{[2-(2-phthalimidoethoxy)ethoxy]methyl}-1,4-dihydropyridine, which is then subjected to the action of sodium ethanolate in the presence of glyme in solution in ethanol to obtain a mixture containing the compound of formula XXII and its homolog substituted at the 5-position with an ethoxycarbonyl radical, which is then subjected to the action of carbonyldiimidazole in solution in a halogenated alkane at room temperature to obtain a mixture containing (−)-4-(2,3-dichlorophenyl)-3-ethoxycarbonyl-5-methoxycarbonyl-6-methyl-2-{[2-(2-phthalimidoethoxy)ethoxy]methyl}-1,4-dihydropyridine, the compound of formula XXIII:

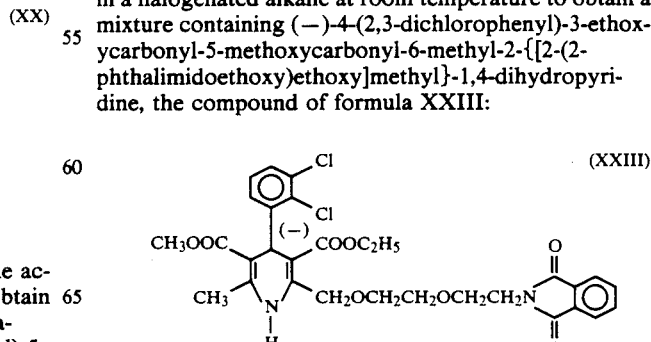
(XXIII)

and its homolog substituted at the 5-position with an ethoxycarbonyl radical, which mixture is then separated by (reverse phase) HPLC to obtain (−)-4-(2,3-dichlorophenyl)-3-ethoxycarbonyl-5-methoxycarbonyl-6-methyl-2-{[2-(2-phthalimidoethoxy)ethoxy]methyl}-1,4-dihydropyridine, which is then brought to reflux in ethanol in the presence of hydrazine hydrate to give the compound of formula XXIV, which can then be salified with a pharmaceutically-compatible organic or inorganic acid.

* * * * *

UNITED STATES PATENT AND TRADEMARK OFFICE
CERTIFICATE OF CORRECTION

PATENT NO. : 4,983,740

DATED : Jan. 8, 1991

INVENTOR(S) : Jean L. Peglion, Yves M. Gargouil, Jean P. Vilaine

It is certified that error appears in the above-identified patent and that said Letters Patent is hereby corrected as shown below:

Column 8, approximate line 46; "(2carboxyp-" should read
-- (2-carboxyp- --.
Column 11, line 39; "1 1" should read -- 1 liter --.
Column 11, line 40; "ether are" should read -- ether, is --.
Column 14, line 64; "1 1" should read -- 1 liter --.
Column 15, approximate line 29; "the", second occurrence
   should read -- then --.
Column 15, Table near the end of the column, first entry under
   the heading "Cl"; "14/54" should read -- 14.54 --.
Column 19, Table at the top of the column, first entry under the
   heading "H"; "3.82" should read -- 5.36 --.
Column 19, Table near the middle of the column, first entry under
   heading "H"; "9.96" should read -- 6.96 --.
Column 27, line 17; "1 1" should read -- 1 liter --.
Column 27, line 61; "1 1" should read -- 1 liter --.
Column 41/42, Table I, Example 4, under the "n" column;
   "H" should read -- 2 --.
Column 41/42, Table I, Example 4, under the "$R_2$" column; insert -- H --.
Column 43/44, Table I, Example 5, under the last column, 6th line;
   "7 14 7.6 ppm," should read -- 7-7.6 ppm,--.
Column 43/44, Table I, Example 8, last column, under the last
   line; insert -- exchangeable --.

UNITED STATES PATENT AND TRADEMARK OFFICE
CERTIFICATE OF CORRECTION

PATENT NO. : 4,983,740

DATED : Jan. 8, 1991

INVENTOR(S) : Jean L. Peglion, Yves M. Gargouil, Jean P. Vilaine

It is certified that error appears in the above-identified patent and that said Letters Patent is hereby corrected as shown below:

Column 51/52, Table I, Example 22, last column, 6th line; "2,1H;" should read -- s,1H; --.
Column 51/52, Table I, Example 23, last column, 4th line; after "4H" insert -- ; --.
Column 53/54, Table I, Example 28, last column, after the 6th line, insert the line -- ppm,$\underline{m}$,3H; 7-8 ppm,4H --.
Column 55/56, Table I, Example 31, last column, between lines 6 and 7, delete "14".
Column 59/60, Table I, Example 37, last column, 2nd line; after "$\underline{m}$," insert -- 10H; 1,2-2,1 ppm,$\underline{m}$, --.
Column 67, line 13; "VII These" should read -- VII. These --.
Column 67, approximate line 35; "bood" should read -- blood --.

Signed and Sealed this

Eighth Day of September, 1992

Attest:

DOUGLAS B. COMER

Attesting Officer     Acting Commissioner of Patents and Trademarks